United States Patent [19]

Kennis et al.

[11] Patent Number: 5,256,659
[45] Date of Patent: Oct. 26, 1993

[54] 2-AMINOPYRIMIDINONE DERIVATIVES

[75] Inventors: Ludo E. J. Kennis, Turnhout; Jan Vandenberk, Beerse; Jozef M. Boey, Vosselaar, all of Belgium

[73] Assignee: Janssen Pharmaceutica N.V., Beerse, Belgium

[21] Appl. No.: 901,465

[22] Filed: Jun. 19, 1992

Related U.S. Application Data

[60] Division of Ser. No. 643,867, Jan. 18, 1991, Pat. No. 5,140,029, which is a continuation-in-part of Ser. No. 456,319, Dec. 26, 1989, abandoned.

[30] Foreign Application Priority Data

Jan. 9, 1989 [GB] United Kingdom ............... 8900382

[51] Int. Cl.$^5$ ................. A61K 31/505; C07D 471/04; C07D 487/04
[52] U.S. Cl. .................... 514/258; 544/256; 544/263; 544/279; 544/281
[58] Field of Search .............. 544/256, 263, 279, 281; 514/258

[56] References Cited

U.S. PATENT DOCUMENTS 4,804,663 2/1989 Kennis et al. .................. 514/258

Primary Examiner—Mukund J. Shah
Assistant Examiner—Y. N. Gupta
Attorney, Agent, or Firm—Charles J. Metz

[57] ABSTRACT

2-Amino-pyrimidininone derivatives possessing serotonin-antagonistic and antihistaminic properties. Compositions containing these compounds as the active ingredient. Method of treating subjects suffering from diseases and/or disorders associated with the release of neurotransmitters, in particular, a method of treating subjects suffering from sleep disorders with 2-aminopyrimidinone derivatives substituted with a 4-bis-(aryl)methylene-1-piperidinyl group; and a method of treating subjects suffering from psychotic diseases and/or disorders with 2-aminopyrimidinone derivatives substituted with a 4-arylcarbonyl-1-piperidinyl, 4-benzazolyl-1-piperidinyl, 4-benzazolyl-1-piperazinyl or 4-indolyl-1-piperidinyl, 4-benzo[b]furanyl-1-piperidinyl or 4-benzo[b]thienyl-1-piperidinyl group.

8 Claims, No Drawings

2-AMINOPYRIMIDINONE DERIVATIVES

CROSS-REFERENCE TO RELATED APPLICATIONS

This application is a division of copending application Ser. No. 07/643,867, filed Jan. 18, 1991, now U.S. Pat. No. 5,140,029, which in turn was a continuation-in-part of application Ser. No. 07/456,319, filed Dec. 26, 1989, now abandoned.

BACKGROUND OF THE INVENTION

In U.S. Pat. Nos. 4,452,799; 4,524,206 and 4,590,196 there are described a number of 3-piperazinyl-1,2-benzisoxazoles and -1,2-benzisothiazoles having psychotropic, tranquilizing and analgesic properties. In EP-A-0,196,132, published Oct. 1, 1986 and J. Med. Chem. 1985, 28, 761–769, there are described 3-piperidinyl-1,2-benzisoxazoles and -1,2-benzisothiazoles as antipsychotics and in EP-A-0,135,781, published Apr. 3, 1985, there are disclosed a number of 3-piperidinyl-indazole derivatives having antipsychotic and analgesic properties. Other structurally related piperidinyl derivatives are described in U.S. Pat. Nos. 4,335,127 and 4,485,107.

The present compounds differ therefrom by the fact that they are invariably substituted with a 2-aminopyrimidininone containing moiety and that a number of them show antihistaminic activity.

DESCRIPTION OF THE INVENTION

The present invention is concerned with novel 2-aminopyrimidinone derivatives having the formula

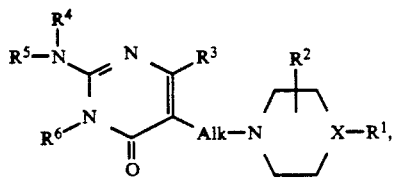
(I)

the pharmaceutically acceptable acid addition salts thereof, and the stereochemically isomeric forms thereof, wherein
$R^1$ is a radical of formula

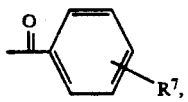
(a-1)

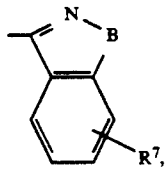
(a-2)

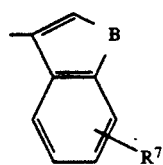
(a-3)

or

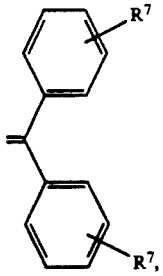
(a-4)

$R^7$ is hydrogen, $C_{1-4}$alkyl or halo;
B is O, S or $NR^8$; wherein $R^8$ is hydrogen, $C_{1-4}$alkyl or Ar-$C_{1-4}$alkyl;
X is CH in case $R^1$ is a radical of formula (a-1), (a-2) or (a-3);
X is C in case $R^1$ is a radical of formula (a-4); or
X may also be N in case $R^1$ is a radical of formula (a-2);
$R^2$ is hydrogen or $C_{1-6}$alkyl;
Alk is $C_{1-6}$alkanediyl;
$R^3$ is hydrogen or $C_{1-6}$alkyl;
$R^4$ is hydrogen, $C_{1-6}$alkyl optionally substituted with $C_{1-6}$alkyloxy, Ar, pyridinyl, furanyl or 5-methyl-2-furanyl;
$R^5$ is hydrogen, $C_{1-6}$alkyl, $C_{1-6}$alkylaminocarbonyl, Ar-aminocarbonyl, $C_{1-6}$alkylcarbonyl or Ar-carbonyl;
$R^6$ is hydrogen, $C_{1-6}$alkyl or Ar-$C_{1-6}$alkyl; or
$R^5$ and $R^6$ taken together may form a bivalent radical of formula

| | |
|---|---|
| $-CH_2-CH_2-$ | (b-1), |
| $-CH_2-CH_2-CH_2-$ | (b-2), |
| $-CH=CH-$ | (b-3), |
| $-CH=N-$ | (b-4), |
| $-N=CH-$ | (b-5) | or

| | |
|---|---|
| $-N=CH-CH_2-$ | (b-6), | wherein one or where possible two hydrogen atoms of said radicals (b-1) to (b-6) each independently from one another may be replaced by $C_{1-6}$alkyl; or wherein one hydrogen atom of radical (b-3) may be replaced by phenyl; each Ar independently is phenyl optionally substituted with 1,2 or 3 substituents each independently selected from halo, hydroxy, nitro, cyano, trifluoromethyl, $C_{1-6}$alkyl, $C_{1-6}$alkyloxy, $C_{1-6}$alkylthio, mercapto, amino, mono- and di($C_{1-6}$alkyl)amino, carboxyl, $C_{1-6}$alkyloxycarbonyl and $C_{1-6}$alkylcarbonyl.

The compounds of formula (I) wherein $R^4$, $R^5$, $R^6$ and/or $R^8$ are hydrogen may also exist in their tautomeric forms. Such forms although not explicitly indicated in the above formula are intended to be included within the scope of the present invention.

As used in the foregoing definitions halo is generic to fluoro, chloro, bromo and iodo; $C_{1-4}$alkyl defines straight and branch chained saturated hydrocarbon radicals having from 1 to 4 carbon atoms such as, for example, methyl, ethyl, 1-methylethyl, 1,1-dimethylethyl, propyl, 2-methylpropyl, butyl and the like;

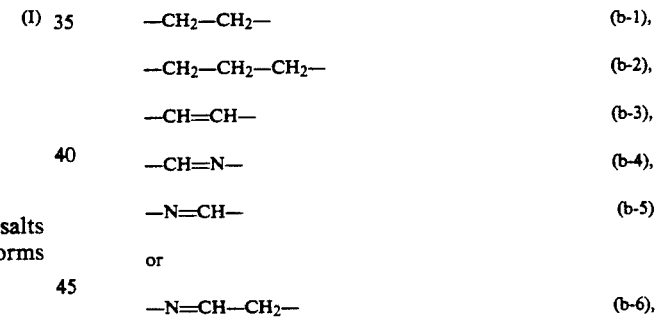

$C_{1-6}$alkyl defines $C_{1-4}$alkyl radicals as defined hereinabove, and the higher homologs thereof having from 5 to 6 carbon atoms; $C_{1-6}$alkanediyl defines bivalent straight or branch chained hydrocarbon radicals containing form 1 to 6 carbon atoms such as, for example, 1,2-ethanediyl, 1,3-propanediyl, 1,4-butanediyl, 1,5-pentanediyl, 1,6-hexanediyl and the branched isomers thereof.

Said acid addition salts as mentioned hereinabove are meant to comprise the therapeutically active non-toxic addition salt forms which the compounds of formula (I) are able to form. The latter can conveniently be obtained by treating the base form with such appropriate acids as inorganic acids, for example, hydrohalic acids, e.g. hydrochloric, hydrobromic and the like, sulfuric acid, nitric acid, phosphoric acid and the like; or organic acids, for example, acetic, propanoic, hydroxyacetic, 2-hydroxypropanoic, 2-oxopropanoic, ethanedioic, propanedioic, butanedioic, (Z)-2-butenedioic, (E)-2-butenedioic, 2-hydroxybutanedioic, 2,3-dihydroxybutanedioic, 2-hydroxy-1,2,3-propanetricarboxylic, methanesulfonic, ethanesulfonic, benzenesulfonic, 4-methylbenzenesulfonic, cyclohexanesulfamic, 2-hydroxybenzoic, 4-amino-2-hydroxybenzoic and the like acids. Conversely the salt form can be converted by treatment with alkali into the free base form.

The term acid addition salt also comprises the hydrates and solvent addition forms which the compounds of formula (I) are able to form. Examples of such forms are e.g. hydrates, alcoholates and the like.

From formula (I) it is evident that the compounds of this invention may have several asymmetric carbon atoms in their structure. Each of these chiral centers may be indicated by the stereochemical descriptors R and S, this R and S notation corresponding to the rules described in Pure Appl. Chem., 1976, 45, 11–30. Unless otherwise mentioned or indicated, the chemical designation of compounds denotes the mixture of all possible stereochemically isomeric forms, said mixtures containing all diastereomers and enantiomers of the basic molecular structure. Stereochemically isomeric forms of the compounds of formula (I) are obviously intended to be embraced within the scope of the invention.

Diastereoisomers may be separated by physical separation methods such as selective crystallization and chromatographic techniques, e.g., counter current distribution, liquid chromatography and the like; and enantiomers may be separated from each other following art-known resolution methods, for example, by the selective crystallization of their diastereomeric salts with optically active acids, or by chromatographic techniques, e.g. by liquid chromatography using a chiral stationary phase.

Pure stereochemically isomeric forms may also be derived from the corresponding pure stereochemically isomeric forms of the appropriate starting materials, provided that the reaction occurs stereospecifically. Preferably, if a specific stereoisomer is desired, said compound will be synthesized by stereoselective methods of preparation. These methods will advantageously employ enantiomerically pure starting materials.

A first subgroup of compounds of formula (I) comprises those compounds wherein
   $R^1$ is a radical of formula (a-4) and
   X is C.
Particular compounds among the compounds of said first subgroup are those wherein
   $R^2$ is hydrogen; and/or
   Alk is $C_{2-4}$alkanediyl; and/or
   $R^3$ is $C_{1-4}$alkyl; and/or
   $R^4$ is hydrogen or $C_{1-6}$alkyl optionally substituted with Ar; and/or
   $R^5$ is hydrogen, $C_{1-6}$alkyl, $C_{1-6}$alkylaminocarbonyl, Ar-aminocarbonyl, $C_{1-6}$alkylcarbonyl or Ar-carbonyl; and/or
   $R^6$ is $C_{1-6}$alkyl; or
   $R^5$ and $R^6$ taken together may form a bivalent radical of formula (b-1) to (b-6), wherein one hydrogen atom of said radicals (b-1) to (b-6) may be replaced by $C_{1-6}$alkyl; or wherein one hydrogen atom of radical (b-3) may be replaced by phenyl; and/or
   $R^7$ is halo; and/or
   each Ar independently is phenyl optionally substituted with 1 or 2 substituents each independently selected from halo, hydroxy, nitro, cyano, trifluoromethyl, $C_{1-6}$alkyl or $C_{1-6}$alkyloxy.

More particular compounds are those particular compounds wherein
   $R^3$ is methyl; and/or
   $R^4$ is hydrogen, $C_{1-6}$alkyl or phenylmethyl; and/or
   $R^5$ is hydrogen, $C_{1-4}$alkyl, methylaminocarbonyl, phenylaminocarbonyl, acetyl or phenylcarbonyl; and/or
   $R^6$ is $C_{1-6}$alkyl; or
   $R^5$ and $R^6$ taken together may form a bivalent radical of formula (b-1), (b-2), (b-3), (b-5) or (b-6), wherein one hydrogen atom of said radicals (b-3), (b-5) and (b-6) may be replaced by methyl; or wherein one hydrogen atom of said radical (b-3) may be replaced by phenyl; and/or
   $R^7$ is fluoro; and/or
   each Ar independently is phenyl optionally substituted with halo or $C_{1-6}$alkyloxy.

The most interesting compounds within the first subgroup of the compounds of formula (I) are 5-[2-[4-[bis(4-fluorophenyl)methylene]-1-piperidinyl]ethyl]-3,6-dimethyl-2-(methylamino)-4(3H)-pyrimidinone and the pharmaceutically acceptable acid addition salts thereof.

A second subgroup of compounds of formula (I) comprises those compounds wherein
   $R^1$ is a radical of formula (a-1), (a-2) or (a-3) and
   X is CH or
   X is N in case $R^1$ is a radical of formula (a-2).
Particular compounds among the compounds of said second subgroup are those wherein
   $R^2$ is hydrogen; and/or
   Alk is $C_{2-4}$alkanediyl; and/or
   $R^3$ is $C_{1-4}$alkyl; and/or
   $R^4$ is hydrogen, $C_{1-6}$alkyl optionally substituted with Ar or pyridinyl; and/or
   $R^5$ is hydrogen, $C_{1-6}$alkyl, $C_{1-6}$alkylaminocarbonyl, Ar-aminocarbonyl, $C_{1-6}$alkylcarbonyl or Ar-carbonyl; and/or
   $R^6$ is $C_{1-6}$alkyl; or
   $R^5$ and $R^6$ taken together may form a bivalent radical of formula (b-1) to (b-6), wherein one hydrogen atom of said radicals (b-1) to (b-6) may be replaced by $C_{1-6}$alkyl; or wherein one hydrogen atom of radical (b-3) may be replaced by phenyl; and/or
   $R^7$ is hydrogen or halo; and/or
   each Ar independently is phenyl optionally substituted with 1 or 2 substituents each independently selected from halo, hydroxy, nitro, cyano, trifluoromethyl, $C_{1-6}$alkyl or $C_{1-6}$alkyloxy.

More particular compounds are those particular compounds wherein $R^3$ is methyl; and/or $R^4$ is hydrogen, $C_{1-6}$alkyl, phenylmethyl or pyridinylmethyl; and/or $R^5$ is hydrogen, $C_{1-6}$alkyl, methylaminocarbonyl, phenylaminocarbonyl, acetyl or phenylcarbonyl; and/or $R^6$ is $C_{1-6}$alkyl; and/or $R^5$ and $R^6$ taken together may form a bivalent radical of formula (b-1), (b-2), (b-3), (b-5) or (b-6), wherein one hydrogen atom of said radicals (b-3), (b-5) and (b-6) may be replaced by methyl; or wherein one hydrogen atom of said radical (b-3) may be replaced by phenyl; and/or $R^7$ is hydrogen or fluoro; and/or each Ar independently is phenyl optionally substituted with halo or $C_{1-6}$alkyloxy.

In order to simplify the structural representations of some of the compounds and intermediates in the following preparations the 2-aminopyrimidinone moiety wherein $R^3$, $R^4$, $R^5$, $R^6$ and Alk are as defined under formula (I) will hereinafter be represented by the symbol L.

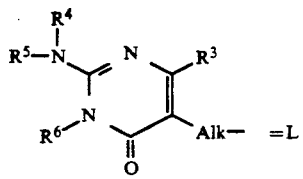

The compounds of formula (I) can generally be prepared by reacting an alkylating reagent of formula L-W (II) with a piperidine (X=CH or C) or a piperazine (X=N) of formula (III). In formula (II) W represents a reactive leaving group such as, for example, halo, e.g., chloro, bromo or iodo, or a sulfonyloxy group, e.g. methanesulfonyloxy, 4-methylbenzenesulfonyloxy and the like leaving groups.

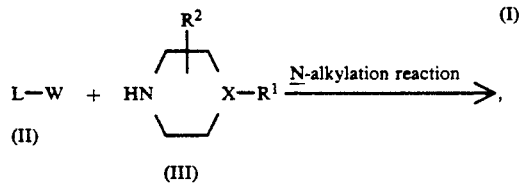

Said N-alkylation reaction can conveniently be conducted in a reaction-inert solvent such as, for example, an aromatic hydrocarbon, e.g., benzene, methylbenzene, dimethylbenzene and the like; a lower alkanol, e.g. methanol, ethanol, 1-butanol and the like; a ketone, e.g., 2-propanone, 4-methyl-2-pentanone and the like; an ether, e.g., 1,4-dioxane, 1,1'-oxybisethane, tetrahydrofuran and the like; a dipolar aprotic solvent, e.g. N,N-dimethylformamide, N,N-dimethylacetamide, nitrobenzene, 1-methyl-2-pyrrolidinone and the like; or a mixture of such solvents. The addition of an appropriate base such as, for example, an alkali or an earth alkaline metal carbonate, hydrogen carbonate, hydroxide, alkoxide or hydride, e.g., sodium carbonate, sodium hydrogen carbonate, potassium carbonate, sodium hydroxide, sodium methoxide, sodium hydride and the like, or an organic base such as, for example an amine, e.g., N,N-diethylethanamine, N-(1-methylethyl)-2-propanamine, 4-ethylmorpholine and the like, may be utilized to pick up the acid which is liberated during the course of the reaction. In some circumstances the addition of a iodide salt, preferably an alkali metal iodide, is appropriate. Somewhat elevated temperatures may enhance the rate of the reaction.

In this and the following preparations, the reaction products may be isolated from the reaction mixture and, if necessary, further purified according to methodologies generally known in the art, such as, for example, extraction, destillation, crystallization, trituration and chromatography.

The compounds of formula (I) wherein $R^1$ is a radical of formula (a-1) and X is CH, said compounds being represented by formula (I-a-1) can also be prepared by hydrolysis of an acetal of formula (IV) wherein each R represents $C_{1-6}$alkyl, or both R radicals taken together form a bivalent $C_{2-3}$alkanediyl radical thus forming a cyclic acetal.

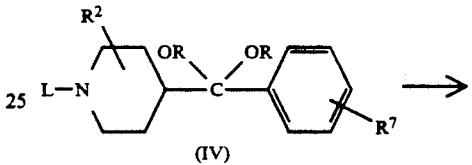

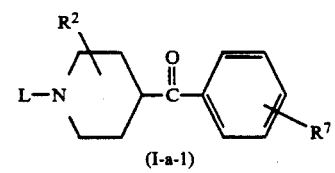

Said hydrolysis can conveniently be conducted by stirring the acetal in an aqueous acidic medium and optionally heating the reaction mixture.

The compounds of formula (I) wherein X is CH and $R^1$ is a radical of formula (a-2) wherein B is O, said compounds being represented by formula (I-a-2-I) can also be prepared by cyclizing an oxime of formula (V), wherein Y is a reactive leaving group, such as, for example, halo or nitro. Preferably Y is a halo group and more particularly fluoro.

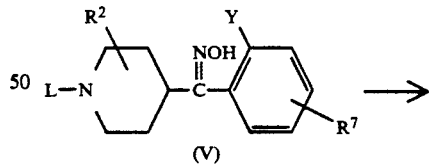

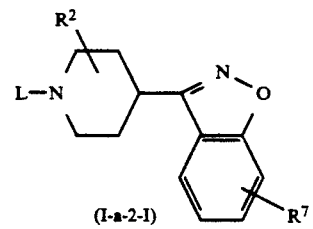

Said cyclization reaction of the oxime of formula (V) may conveniently be conducted by treatment with an appropriate base, preferably in a suitable reaction-inert solvent at temperatures in the range of 20° to 200° C., preferably at 50° to 150° C., and in particular at the reflux temperature of the reaction mixture. Or, if desirable, said base may first be added preferably at room temperature, whereupon the thus formed salt is cyclized, preferably at increased temperature and more preferably at the reflux temperature of the reaction mixture. Appropriate bases are for example, alkali and earth alkaline metal carbonates, hydrogen carbonates, hydroxides, alkoxides, amides or hydrides, e.g., sodium carbonate, sodium hydrogen carbonate, potassium carbonate, sodium hydroxide, sodium methoxide, sodium amide, sodium hydride and the like bases. Suitable solvents for said process are, for example, water; aromatic hydrocarbons, e.g., benzene, methylbenzene, dimethylbenzene and the like; halogenated hydrocarbons, e.g., dichloromethane, trichloromethane, tetrachloromethane, 1,1,1-trichloroethane, 1,2-dichloroethane and the like; lower alkanols, e.g. methanol, ethanol, 1-propanol, 2-propanol, 1-butanol, 1,2,-ethanediol and the like; ketones, e.g., 2-propanone, 4-methyl-2-pentanone and the like; ethers, e.g., 1,1'-oxybisethane, 1,1'-oxybisbutane, 1,4-dioxane, tetrahydrofuran, 1,1'-oxybis[2-methoxyethane] and the like; dipolar aprotic solvents, e.g., N,N-dimethylformamide, N,N-dimethylacetamide, 1-methyl-2-pyrrolidinone, dimethyl sulfoxide, hexamethylphosphoric triamide and the like; or mixtures of said solvents.

The compounds of formula (I-a-2-I) may also be prepared by cyclizing an activated oxime derivative of formula (VI), wherein V is an acid residue and more particularly is ($C_{1-6}$alkyl or aryl)carbonyl, e.g. formyl, acetyl, propionyl, benzoyl and the like; ($C_{1-6}$alkyl or aryl)oxycarbonyl, e.g. methoxycarbonyl, ethoxycarbonyl, (1,1-dimethyl)ethoxycarbonyl, phenyloxycarbonyl and the like; ($C_{1-6}$alkyl or aryl)sulfonyl, e.g. methanesulfonyl, benzenesulfonyl, 4-methylbenzenesulfonyl, 2-naphthalenesulfonyl and the like; N-acylaminocarbonyl, e.g. trichloromethylcarbonylaminocarbonyl and the like.

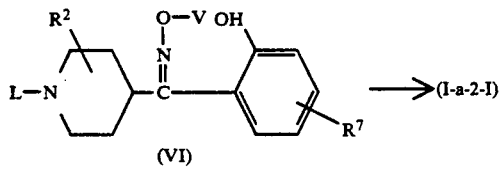

Said cyclization reaction of the activated oxime derivative of formula (VI) may conveniently be conducted by treatment with an appropriate base, preferably in a suitable reaction-inert solvent, at temperatures in the range from 20° to 200° C., particularly from 50° to 150° C. and preferably at the reflux temperature of the reaction mixture. In some instances however, it may be advantageous not to add a base to the reaction mixture and to remove the acid liberated during the reaction by destillation at normal pressure or, if desired, at reduced pressure. Alternatively, said cyclization may also be effected by heating the oxime derivative (VI) in vacuo without a solvent. Appropriate bases are for example, alkali and earth alkaline metal carbonates, hydrogen carbonates and amines, e.g. sodium carbonate, potassium carbonate, sodium hydrogen carbonate, N,N-diethylethanamine, 4-ethylmorpholine, 1,4-diazabicyclo[2.2.2]octane, pyridine and the like bases. Suitable solvents for said cyclization are, for example, aromatic hydrocarbons, e.g., benzene, methylbenzene, dimethylbenzene and the like; ethers, e.g. 1,1'-oxybisethane, 1,1'-oxybisbutane, tetrahydrofuran, 1,4-dioxane, 1,1'-oxybis[2-methoxyethane], 1,2-bis[2-methoxyethoxy]ethane and the like; dipolar aprotic solvents, e.g. N,N-dimethylformamide, N,N-dimethylacetamide, 1-methyl-2-pyrrolidinone, hexamethylphosphoric triamide, pyridine, methylpyridine, dimethylpyridine, acetic anhydride, N-propionic anhydride, N-butyric anhydride and the like; halogenated hydrocarbons, e.g. trichloromethane, tetrachloromethane, 1,2-dichloroethane, 1,1,2,2-tetrachloroethane, chlorobenzene, dichlorobenzene and the like solvents.

The compounds of formula (I) wherein X is CH and $R^1$ is a radical of formula (a-2) wherein B is $NR^8$, said compounds being represented by formula (I-a-2-II) may also be prepared by the cyclization reaction of an intermediate of formula (VII) with an appropriate hydrazine derivative $R^8$-NH-NH$_2$ (VIII) or an acid addition salt thereof.

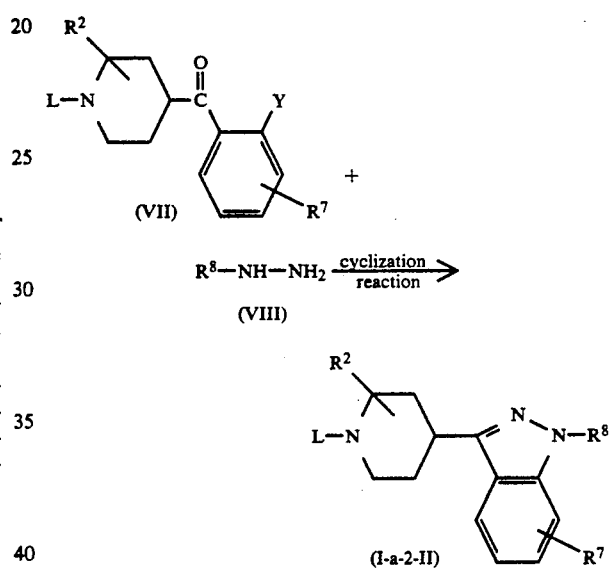

In formula (VII) Y represents an appropriate leaving group such as, for example, halo, e.g. fluoro or chloro; or a nitro group. Said cyclization reaction may be conducted by stirring, and if desired, heating the reactants in a suitable reaction-inert solvent in the presence of an appropriate base. Suitable solvents generally have a relatively high boiling point and are, for example, water; alkanols, e.g. methanol, ethanol, 1-butanol and the like; diols, e.g. 1,2-ethanediol and the like; aromatic hydrocarbons, e.g. benzene, methylbenzene, dimethylbenzene and the like; halogenated hydrocarbons, e.g. trichloromethane, tetrachloromethane and the like; ethers, e.g. tetrahydrofuran, 1,4-dioxane, 1,1'oxybisbutane, 1,1'-oxybis-(2-methoxyethane) and the like; dipolar aprotic solvents, e.g. N,N-dimethyl-formamide, N,N-dimethylacetamide, dimethylsulfoxide and the like; or mixtures of such solvents. Appropriate bases preferably are alkali or earth alkaline metal carbonates or hydrogen carbonates such as, for example, sodium hydrogen carbonate, sodium carbonate, potassium carbonate and the like; or amines such as N,N-diethylethanamine, 4-ethylmorpholine, N-(1-methylethyl)-2-propanamine and the like.

Additionally, the compounds of formula (I-a-2-II) may be prepared by the nitrosation of an intermediate aniline of formula

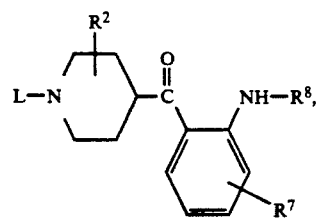

(IX)

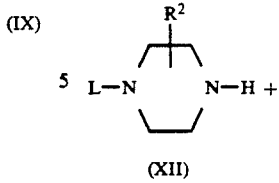

(XII)

with an alkali metal nitrite, e.g. sodium nitrite, in an aqueous acidic medium and treating the thus obtained N-nitroso compound (X-a) or, in case $R^8$ is hydrogen, the diazonium salt (X-b),

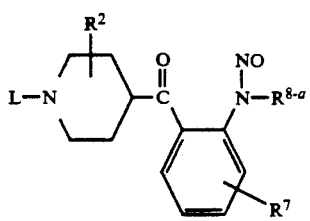

(X-a)

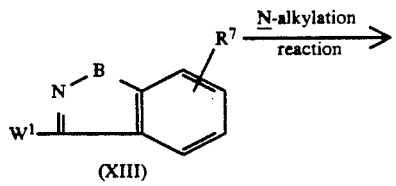

(XIII)

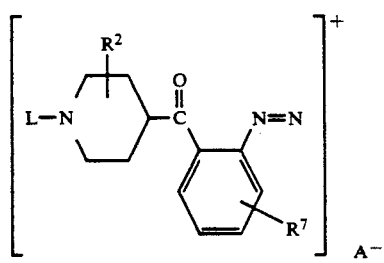

(X-b)

wherein $A^-$ represents the conjugated base of the acid used hereinabove, with an appropriate reducing agent such as, for example, hydrogen in the presence of a hydrogenation metal catalyst, e.g. Raney nickel or Raney cobalt; or a sulfite, e.g. sodium sulfite, thus yielding the corresponding hydrazine derivative of formula

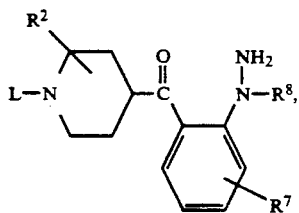

(XI)

which in most instances spontaneously, or if necessary upon increasing the temperature, may cyclize to a compound of formula (I-a-2-II).

The compounds of formula (I) wherein X is N and $R^1$ is a radical of formula (a-2), said compounds being represented by formula (I-a-2-III), may also be prepared by N-alkylating a piperazine derivative of formula (XII) with a benzazole of formula (XIII),

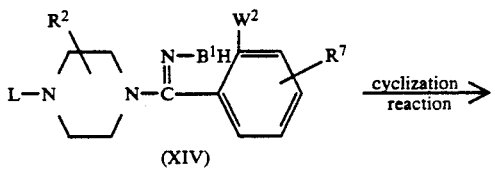

(I-a-2-III)

wherein $W^1$ represents a suitable leaving group such as halo, e.g. chloro or bromo. Said N-alkylation reaction of (XII) with (XIII) may be carried out following the same procedure as described hereinabove for the preparation of compounds of formula (I) from the intermediates (II) and (III).

The compounds of formula (I) wherein X is N and $R^1$ is a radical of formula (a-2) wherein B is O or $NR^8$, said B being represented by $B^1$ and said compounds by formula (I-a-2-IV), can also be obtained by the cyclization of an intermediate of formula (XIV) upon treatment with an appropriate base in a reaction-inert solvent.

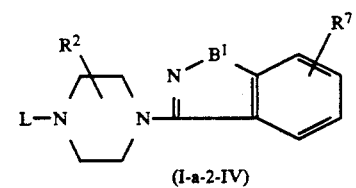

(XIV)

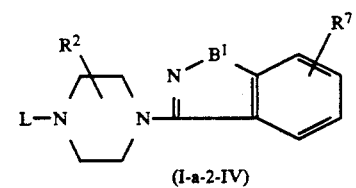

(I-a-2-IV)

In formula (XIV) $W^2$ represents a suitable leaving group such as halo, e.g. fluoro or chloro, or a nitro group. Appropriate bases for said cyclization are, for example, alkali and earth alkaline metal carbonates, hydrogen carbonates, hydroxides, alkoxides or hydrides, e.g. sodium carbonate, sodium hydrogen carbonate, potassium carbonate, sodium hydroxide, sodium methoxide, sodium hydride or organic bases such as amines, e.g. N,N-diethylethanamine, 4-ethylmorpholine and the like bases. Suitable solvents are, for example, aromatic hydrocarbons, e.g. benzene, methylbenzene, dimethylbenzene and the like; lower alkanols, e.g. methanol, ethanol, 1-butanol and the like; ketones, e.g. 2-propanone, 4-methyl-2-pentanone and the like; ethers, e.g. 1,4-dioxane, tetrahydrofuran and the like; dipolar aprotic solvents, e.g. N,N-dimethylformamide, N,N-dimethylacetamide, dimethylsulfoxide, 1-methyl-2-pyrrolidinone and the like or mixtures of such solvents. In order to enhance the rate of the reaction, the temperature of the reaction mixture may be raised and particularly, said cyclization may be conducted at the reflux temperature of the reaction mixture.

The compounds of formula (I-a-2-IV) wherein $B^1$ is O, said compounds being represented by formula (I-a-2-V) can also be obtained by cyclizing an activated oxime derivative of formula (XV),

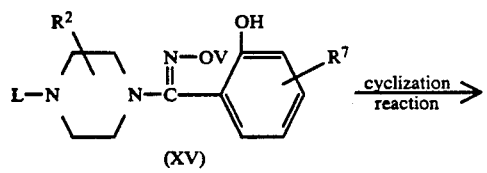

(XV)

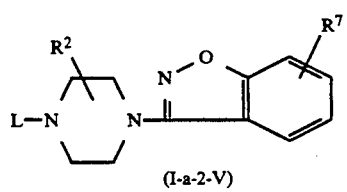

(I-a-2-V)

wherein V is formyl, ($C_{1-6}$alkyl or aryl)carbonyl, e.g. acetyl, propionyl, benzoyl and the like; ($C_{1-6}$alkyl or aryl)oxycarbonyl, e.g. methoxycarbonyl, ethoxycarbonyl, (1,1-dimethyl)ethoxycarbonyl, phenyloxycarbonyl and the like; ($C_{1-6}$alkyl or aryl)sulfonyl, e.g. methanesulfonyl, benzenesulfonyl, 4-methylbenzenesulfonyl, 2-naphthalenesulfonyl and the like; N-acylaminocarbonyl, e.g. trichloromethylcarbonylaminocarbonyl and the like. Said cyclization reaction of the activated oxime derivative of formula (XV) may conveniently be conducted by treatment with an appropriate base, preferably in a suitable reaction-inert solvent, at temperatures in the range from 20° to 200° C., particularly from 50° to 150° C. and preferably at the reflux temperature of the reaction mixture. In some instances however, it may be advantageous not to add a base to the reaction mixture and to remove the acid liberated during the reaction by destillation at normal pressure or, if desired, at reduced pressure. Alternatively, said cyclization may also be effected by heating the oxime derivative (XV) in vacuo without a solvent. Appropriate bases are for example, alkali and earth alkaline metal carbonates, hydrogen carbonates and amines, e.g. sodium carbonate, potassium carbonate, sodium hydrogen carbonate, N,N-diethylethanamine, 4-ethylmorpholine, 1,4-diazabicylco[2.2.2]octane, pyridine and the like bases. Suitable solvents for said cyclization are, for example, aromatic hydrocarbons, e.g. benzene, methylbenzene, dimethylbenzene and the like; ethers, e.g. 1,1'-oxybisethane, 1,1'-oxy-bisbutane, tetrahydrofuran, 1,4-dioxane, 2,2'-oxybis[methoxyethane], 2,5,8,11-tetra-oxadodecane and the like; dipolar aprotic solvents, e.g. N,N-dimethylformamide, N,N-dimethylacetamide,1-methyl-2-pyrrolidinone, hexamethylphosphoric triamide, pyridine, acetic anhydride and the like; halogenated hydrocarbons, e.g. trichloromethane, tetrachloromethane, 1,2-dichloroethane, chlorobenzene and the like solvents.

The compounds of formula (I-a-4) may also be obtained by reacting a 4-piperidone (XVI) with a suitable ylide (XVII) such as, for example, a phosphorane (e.g. $R^9$ and $R^{10}$ are aryl or alkyl; Wittig reaction) or a phosphonate ylide (e.g. $R^9$ is alkyloxy and $R^{10}$ is $O^-$; Horner-Emmons reaction).

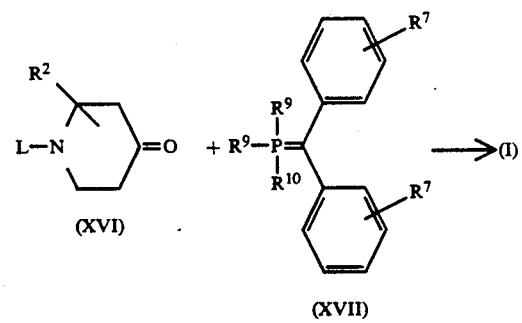

The reaction can conveniently be conducted by treating a phosphonium salt (XVIII: $R^9$ and $R^{10}$ are aryl or alkyl) or a phosphonate (XVIII: $R^9$ is alkyloxy and $R^{10}$ is $O^-$)

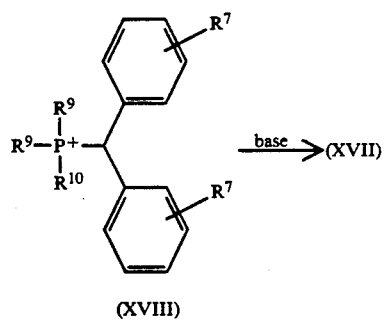

with an appropriate base such as, for example, butyllithium, methyllithium, sodium amide, sodium hydride, sodium or potassium alkoxide, sulfinylbis(methane) sodium salt and the like bases, under an inert atmosphere and in a reaction-inert solvent such as, for example, a hydrocarbon, e.g. hexane, heptane, cyclohexane and the like; an aromatic hydrocarbon, e.g. benzene, methylbenzene and the like; an ether, e.g. 1,1'-oxybisethane, tetrahydrofuran, 1,2-dimethoxyethane and the like; a dipolar aprotic solvent, e.g. dimethylsulfoxide, hexamethylphosphor triamide and the like solvents; and subsequently treating the thus obtained ylide (XVII) with the ketone of formula (XVI), optionally at a slightly enhanced temperature.

Alternatively the compounds of formula (I-a-4) may be prepared by reacting a 4-piperidinone (XVI) with an organometallic reagent of formula (XIX) wherein M represents a metal group such as, for example, lithium, halomagnesium, copper lithium and the like; and subsequently dehydrating the alcohol of formula (XX), for example, by treatment with an appropriate acid, e.g. hydrochloric or sulfuric acid.

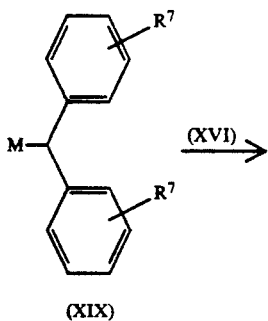

(XIX)

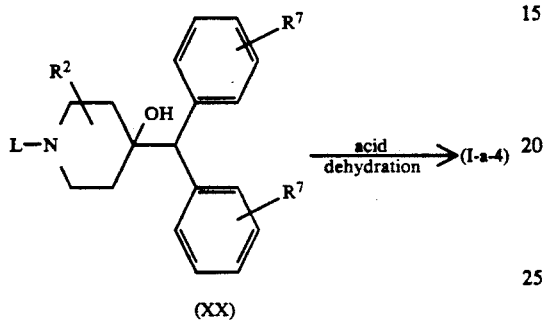

(XX)

The organometallic reagent (XIX) may conveniently be prepared by reacting an appropriate diarylmethylhalogenide with a metal such as lithium or magnesium in a reaction-inert solvent such as, for example, an ether, e.g. 1,1'-oxybisethane, tetrahydrofuran, 1,2-dimethoxyethane and the like.

The compounds of formula (I) can also be converted into each other following art-known procedures of functional group transformation. Some examples of such procedures will be cited hereinafter. Amino groups may be alkylated or acylated following art— known procedures such as, for example, N-alkylation, N-acylation, reductive N-alkylation and the like methods. For example ($C_{1-6}$alkyl or Ar)aminocarbonyl and the like groups may be introduced by reacting the starting amine with an appropriate ($C_{1-6}$alkyl or Ar)isocyanate. The compounds of formula (I) containing an amino group substituted with a radical Ar-$CH_2$, may be hydrogenolyzed by treating the starting compounds with hydrogen in the presence of a suitable catalyst, e.g., palladium-on-charcoal, platinum-on-charcoal, preferably in an alcoholic medium.

A number of intermediates and starting materials in the foregoing preparations are known compounds which may be prepared according to art-known methodologies of preparing said or similar compounds. For example, some of the intermediates of formula (III) and (XIII) and their preparations are described in U.S. Pat. Nos. 4,335,127; 4,485,107; 4,452,799; 4,524,206 and 4,590,196; and in EP-A-0,196,132 and 0,135,781. Other intermediates may be prepared according to art-known methodologies of preparing similar compounds and for some of them, preparative methods are presented hereinafter.

The intermediates of formula (II) can generally be prepared from an appropriate alcohol of formula (XXI) upon treatment with a halogenating reagent such as, for example, a hydrohalic acid, e.g. hydrochloric or hydrobromic acid; thionyl chloride; phosphorous trichloride; phosphoryl chloride; methanesulfonylchloride, triphenylphosphinetetrahalomethane and the like reagents; or with a sulfonylhalide reagent such as, for example, methanesulfonylchloride, 4-methylbenzenesulfonylchloride and the like.

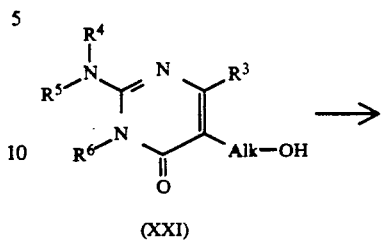

(XXI)

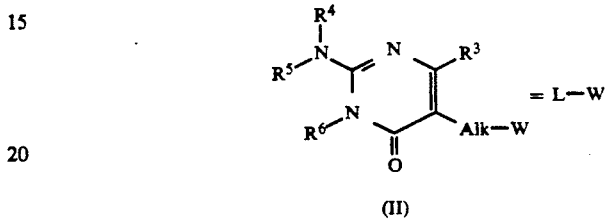

(II)

The intermediates of formula (XXI) wherein $R^5$ and $R^6$ together form a bivalent radical of formula (b-1) to (b-3) can generally be prepared by condensing an intermediate of formula (XXI-a) wherein $R^5$ and $R^6$ are hydrogen with an appropriate alkylating reagent. For example the N-alkylation reaction of intermediate (XXI-a) with a 1,2-dihaloethane or a 1,3-dihalopropane can yield those intermediates wherein $R^5$ and $R^6$ together form an ethanediyl (XXI-b-1) or propanediyl (XXI-b-2) radical.

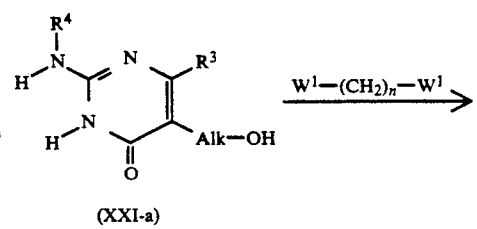

(XXI-a)

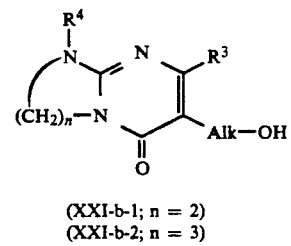

(XXI-b-1; n = 2)
(XXI-b-2; n = 3)

Intermediates of formula (XXI-b-3) can be obtained by condensing (XXI-a) wherein $R^5$ and $R^6$ are hydrogen, with an α-haloketone or -aldehyde (XXII) wherein $R^{11}$ and $R^{12}$ each independently represent hydrogen, $C_{1-6}$alkyl or phenyl, in the presence of an appropriate acid or base.

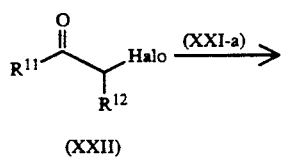

(XXII)

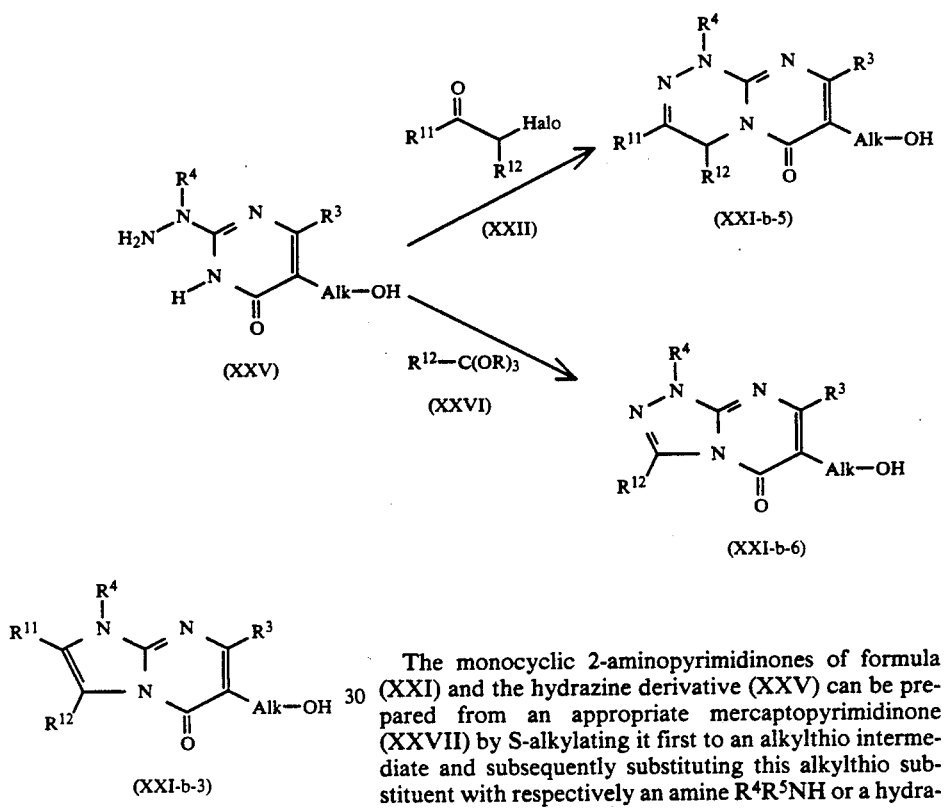

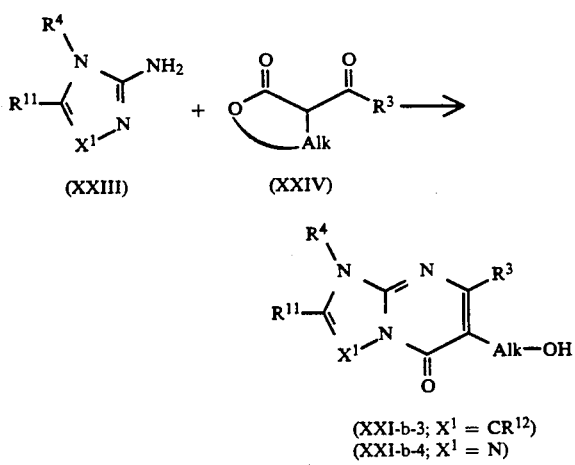

The intermediates of formula (XXI-b-3) and (XXI-b-4) can also be prepared by condensing an appropriately substituted 2-aminoimidazole ($X^1=CR^{12}$) or 2-aminotriazole ($X^1=N$) of formula (XXIII) wherein $R^{11}$ and $R^{12}$ each independently represent hydrogen, $C_{1-6}$alkyl or phenyl, with an α-acyl-lactone (XXIV) in the presence of an activating reagent such as a halogenating reagent in a reaction-inert solvent. In some instances the hydroxy group may be converted in situ into a halo group, thus directly yielding an alkylating reagent of formula (II).

The intermediates of formula (XXI-b-5) and (XXI-b-6) can be obtained by condensing a hydrazine derivative (XXV) with respectively an α-haloketone or -aldehyde (XXII) and an orthoester (XXVI) wherein $R^{11}$ and $R^{12}$ each independently represent hydrogen or $C_{1-6}$alkyl.

The monocyclic 2-aminopyrimidinones of formula (XXI) and the hydrazine derivative (XXV) can be prepared from an appropriate mercaptopyrimidinone (XXVII) by S-alkylating it first to an alkylthio intermediate and subsequently substituting this alkylthio substituent with respectively an amine $R^4R^5NH$ or a hydrazine $R^4NHNH_2$.

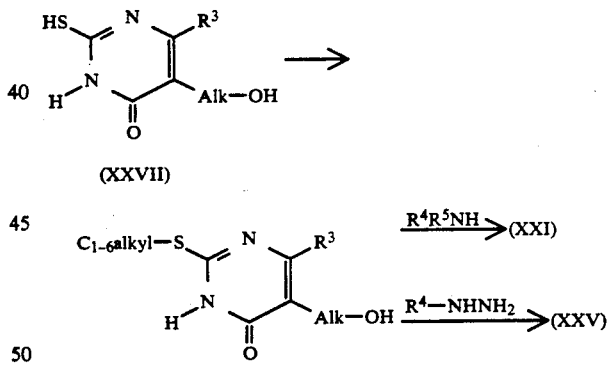

The compounds of formula (I), the pharmaceutically acceptable acid addition salts and stereochemically isomeric forms thereof, are potent antagonists of neurotransmitters and in particular of the mediators serotonin and histamine. Antagonizing said mediators will suppress or relieve a variety of symptoms associated with phenomena induced by the release, in particular the excessive release, of these mediators.

Antihistaminic activity can be demonstrated by, e.g., the results obtained in the "Protection of Rats from Compound 48/80—induced lethality" test described in U.S. Pat. No. 4,556,660. Serotonin-antagonism can be demonstrated in the "Gastric Lesions induced by compound 48/80 in rats" test described in U.S. Pat. No. 4,335,127 and in the "Combined apomorphine, tryptamine and norepinephrine in rats" test described in EP-A-0,196,132.

Therapeutic indications for using the present compounds are mainly in the CNS area, the gastrointestinal and cardiovascular field and related domains.

Some of the compounds of formula (I) are very interesting serotonin antagonists which are useful for influencing the sleep-wakefulness pattern in warm-blooded animals, as can be demonstrated in the test-procedure "Sleep-wakefulness patterns in the rat". More specifically, the compounds wherein $R^1$ is a radical of formula (a-4) and X is C, said compounds being defined as the first subgroup, clearly improve the quality of sleep by increasing the amount of deep slow wave sleep (SWS2). Therapeutic indications for using said compounds are sleep disorders.

On the other hand, some of the compounds of formula (I) have interesting neuroleptic properties, since they show combined antagonism against dopamine, serotonin and histamine. Therapeutic indications for using said compounds, more particularly those compounds wherein $R^1$ is a radical of formula (a-1), (a-2) or (a-3) and X is CH or N, said compounds being defined as the second subgroup, comprise psychotic diseases, aggressive behaviour, anxiety, depression and migraine. Since the instant compounds show combined dopamine-serotonin antagonism, they are expected to be particularly useful in treating patients suffering from schizophrenia by offering relief of both the positive and the negative symptoms of schizophrenia. Further, the present compounds also appear to be useful therapeutic agents for combatting autism. In addition, serotonin antagonists have been associated with a number of other properties such as the suppression of appetite and the promotion of weight loss, which may prove effective in combatting obesity; and also the alleviation of withdrawal symptoms in addicts trying to discontinue the use of drugs such as, for example, alcohol, tobacco, cocaine, opiates, opioids, amphetamines and the like.

In view of their useful pharmacological properties the subject compounds may be formulated into various pharmaceutical forms for administration purposes. To prepare the pharmaceutical compositions of this invention, an effective amount of the particular compound, in base or acid addition salt form, as the active ingredient is combined in intimate admixture with a pharmaceutically acceptable carrier, which carrier may take a wide variety of forms depending on the form of preparation desired for administration. These pharmaceutical compositions are desirably in unitary dosage form suitable, preferably, for administration orally, rectally, percutaneously, or by parenteral injection. For example, in preparing the compositions in oral dosage form, any of the usual pharmaceutical media may be employed such as, for example, water, glycols, oils, alcohols and the like in the case of oral liquid preparations such as suspensions, syrups, elixirs and solutions: or solid carriers such as starches, sugars, kaolin, lubricants, binders, disintegrating agents and the like in the case of powders, pills, capsules and tablets. Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, for example to aid solubility, may be included. Injectable solutions, for example, may be prepared in which the carrier comprises saline solution, glucose solution or a a mixture of saline and glucose solution. Injectable suspensions may also be prepared in which case appropriate liquid carriers, suspending agents and the like may be employed. In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin. Said additives may facilitate the administration to the skin and/or may be helpful for preparing the desired compositions. These compositions may be administered in various ways, e.g., as a transdermal patch, as a spot-on or as an ointment. Acid addition salts of (I) due to their increased water solubility over the corresponding base form, are obviously more suitable in the preparation of aqueous compositions.

It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

In view of the usefulness of the subject compounds in the treatment of diseases associated with the release of neurotransmitters it is evident that the present invention provides a method of treating warm-blooded animals suffering from such diseases, more in particular from sleep-disorders or psychotic diseases, said method comprising the systemic administration of a pharmaceutically effective amount of a compound of formula (I) or a pharmaceutically acceptable acid addition salt thereof in admixture with a pharmaceutical carrier. Those of skill in the treatment of diseases associated with the release of neurotransmitters could easily determine the effective amount from the test results presented here. In general it is contemplated that an effective amount would be from 0.01 mg/kg to 4 mg/kg body weight, preferably from 0.04 mg/kg to 2 mg/kg body weight.

The following examples are intended to illustrate and not to limit the scope of the present invention in all its aspects. Unless otherwise stated all parts therein are by weight.

EXPERIMENTAL PART

A. Preparation of Intermediates

Example 1 a) To a stirred suspension of 90 parts of 5-(2-hydroxyethyl)-2-mercapto-6-methyl-4(3$\underline{H}$)-pyrimidinone in 320 parts of methanol were added 90 parts of a sodium methoxide solution 30%. After stirring for 20 minutes, 72 parts of iodomethane were added and the whole was stirred and refluxed for 3 hours. The reaction mixture was evaporated in vacuo and water was added to the residue. The precipitated product was filtered off and crystallized from ethanol, yielding 78 parts (78%) of 5-(2-hydroxyethyl)-6-methyl-2-(methylthio)-4(3$\underline{H}$)-pyrimidinone (interm. 1).

b) A mixture of 160 parts of interm. 1 and ±700 parts of methanamine monoacetate was refluxed for 2 hours. After cooling to 50° C., nitrogen was bubbled through the solution for 1 hour. The reaction mixture was cooled to 10° C. and the whole was poured into 2000 parts of ice water and 100 parts of ammonium hydroxide were added. After 30 minutes, a solid product was filtered off, washed twice with 200 parts of water and twice with 80 parts of acetonitrile and dried, yielding 108.5 parts (74.0%) of 5-(2-hydroxyethyl)-6-methyl-2-(methylamino)-4(3H)-pyrimidinone (interm. 2).

c) To a stirred mixture of 50.7 parts of interm. 2, 31.8 parts of sodium carbonate and 376 parts of N,N-dimethylformamide were added at once 27.75 parts of 1-chloro-2-propanone. The reaction mixture was stirred first for 2 hours at 100° C. and then overnight at room temperature. The precipitate was filtered off and the filtrate was evaporated. The residue was treated with 160 parts of acetonitrile. After cooling to 0° C., the product was filtered off and dried, yielding 32 parts (48.5%) of 5-(2-hydroxyethyl)-6-methyl-2-(methylamino)-3-(2-oxopropyl)-4(3H)-pyrimidinone (interm. 3).

d) A solution of 38.3 parts of interm. 3 and 250 parts of acetic acid, saturated with hydrogen bromide was stirred overnight at reflux temperature. The solvent was evaporated and the residue was combined with 375 parts of a hydrobromic acid solution 48% in water. The whole was stirred for 5 hours at reflux temperature. After evaporation, the residue was combined with 400 parts of water and treated with 100 parts of an ammonium hydroxide solution. The precipitated product was filtered off, washed with 40 parts of cooled ethanol and dried, yielding 34 parts (74.8%) of 6-(2-bromoethyl)-1,2,7-trimethyl-1H,5H-imidazo[1,2-a]pyrimidin-5-one; mp. 125° C. (interm. 4).

In a similar manner there was also prepared 6-(2-bromoethyl)-1,7-dimethyl-2-phenylimidazo[1,2-a]pyrimidin-5(1H)-one; mp. 150° C. (interm. 5).

Example 2 a) To a stirred mixture of 64 parts of interm. 2, 80.6 parts of sodium carbonate and 329 parts of N,N-dimethylformamide were added 54.5 parts of 1-bromo-2-chloroethane. The reaction mixture was heated for 20 hours at 100° C. After cooling, the precipitate was filtered off and the filtrate was evaporated. The residue was extracted with 450 parts of trichloromethane. The extract was washed twice with 50 parts of water, dried, filtered and evaporated, yielding 15.2 parts (20.8%) of 2,3-dihydro-6-(2-hydroxyethyl)-1,7-dimethyl-1H,5H-imidazo[1,2-a]pyrimidin-5-one as a residue (interm. 6).

b) A mixture of 15.2 parts of interm. 6, 32.4 parts of thionyl chloride and 300 parts of trichloromethane was stirred for 2 hours at reflux temperature. The reaction mixture was evaporated and the residue was treated with 40 parts of acetonitrile. The product was filtered off and dried, yielding 13.2 parts (69.5%) of 6-(2-chloroethyl)-2,3-dihydro-1,7-dimethyl-1H,5H-imidazo[1,2-a]pyrimidin-5-one monohydrochloride; mp. 220° C. (interm. 7).

Example 3 a) A mixture of 43 parts of benzenemethanamine and 77 parts of interm. 1 was stirred for 5 hours in an oil bath at 150°-160° C. After cooling, the precipitated product was stirred in water. The product was filtered off, washed twice with water and crystallized from ethanol, yielding 78 parts (79%) of 5-(2-hydroxyethyl)-6-methyl-2-[(phenylmethyl)-amino]-4(3H)pyrimidinone; mp. 187.3° C. (interm. 8).

b) To a stirred suspension of 137 parts of interm. 8 in 564 parts of iodomethane were added 90 parts of N,N-dimethylformamide. The mixture was stirred for 30 minutes at room temperature and 71 parts of a sodium methoxide solution 30% were added (exothermic reaction, the temperature rose from 22° C.→40° C.). The reaction mixture was stirred for 2 hours. The reaction mixture was evaporated under reduced pressure and the residue was treated with 1000 parts of water. The solid product was filtered off and crystallized twice: first from 80 parts of acetonitrile and then from 640 parts of acetonitrile. After cooling to 0° C., the product was filtered off and dried, yielding 81.4 parts (59.6%) of 5-(2-hydroxyethyl)-3,6-dimethyl-2-[(phenylmethyl)amino]-4(3H)-pyrimidinone (interm. 9). Following the procedures described in example 1c,d hereinabove, intermediate 8 was converted into 6-(2-bromoethyl)-2,7-dimethyl-1-(phenylmethyl)imidazo[1,2-a]pyrimidin-5(1H)-one monohydrobromide (interm. 10).

Following the procedure described in example 2b hereinabove, intermediate 9 was converted into 5-(2-chloroethyl)-3,6-dimethyl-2-[(phenylmethyl)amino]-4(3H)-pyrimidinone monohydrochloride (interm. 11).

Example 4

To a stirred mixture of 67.7 parts of 2-amino-5-(2-hydroxyethyl)-6-methyl-4(3H)-pyrimidinone and 800 parts of ethanol were added 80 parts of a sodium methoxide solution 30%. The reaction mixture was heated to reflux temperature and 62.5 parts of iodomethane were added dropwise. Upon complete addition, stirring was continued for 4 hours at reflux temperature. The reaction mixture was evaporated and the residue was suspended in 400 parts of water. The precipitated product was filtered off, washed with 40 parts of ethanol and dried, yielding 58.3 parts (79.6%) of 2-amino-5-(2-hydroxy-ethyl)-3,6-dimethyl-4(3H)-pyrimidinone (interm. 12).

Following the procedure described in example 2b hereinabove, intermediate 12 was converted into 2-amino-5-(2-chloroethyl)-3,6-dimethyl-4(3H)-pyrimidinone monohydrochloride (interm. 13).

In a similar manner there were also prepared 2-amino-5-(2-chloroethyl)-3-ethyl-6-methyl-4(3H)-pyrimidinone monohydrochloride (interm. 14) and 2-amino-5-(2-chloroethyl)-6-methyl-3-propyl-4(3H)-pyrimidinone monohydrochloride (interm. 15).

Example 5 a) A mixture of 200 parts of 2-amino-3-(2-hydroxyethyl)-3,6-dimethyl-4(3H)-pyrimidinone, 210 parts of acetic acid and 1350 parts of acetic acid anhydride was stirred for 5 hours at reflux temperature. After cooling, the reaction mixture was evaporated in vacuo and the residue was solidified while stirring in a mixture of ethyl acetate and 2,2'-oxybispropane (1:1 by volume). The solid product was filtered off (the filtrate was set aside), washed with 2,2'-oxybispropane and dried, yielding a first fraction of 134 parts (45.9%) of 2-(acetylamino)-1,2-dihydro-1,4-dimethyl-6-oxo-5-pyrimidineethanol acetate(ester). The filtrate, which was set aside was cooled at −10° C. The precipitated product was filtered off and dried, yielding a second fraction of 156 parts (53.4%) of 2-(acetylamino)-1,2-dihydro-1,4-dimethyl-6-oxo-5-pyrimidineethanol acetate(ester). Total yield: 190 parts (99.3%) of 2-(acetylamino)-1,2-dihydro-1,4-dimethyl-6-oxo-5-pyrimidineethanol acetate(ester) (interm. 16).

b) 19.8 Parts of a sodium hydride dispersion 50% were suspended twice in 64 parts of petroleum ether and the solvent was decanted each time. A sodium hydride dispersion 50% was stirred in 94 parts of N,N-dimethylformamide under nitrogen atmosphere. A mixture of 88.2 parts of interm. 16 and 282 parts of N,N-dimethylformamide was added dropwise to the previous mixture at <15° C. Upon complete addition, stirring was continued for 30 minutes. 57 Parts of iodomethane were added dropwise at room temperature. The reaction mixture was stirred for 10 minutes at 50° C. After cooling to 10° C., the precipitate was filtered off and the filtrate was evaporated. The residue was taken up in 300 parts of water and 63.5 parts of hydrochloric acid and the whole was stirred for 3 hours at reflux temperature. The whole was evaporated, the residue was taken up in 300 parts of water and treated with ammonium hydroxide. The precipitated product was filtered off, washed with 40 parts of acetonitrile and dried, yielding 35.7 part (54.8%) of 5-(2-hydroxyethyl)-3,6-dimethyl-2-(methylamino)-4(3H)-pyrimidinone (interm. 17).

Following the procedure described in example 2b hereinabove, intermediate 17 was converted into 5-(2-chloroethyl)-3,6-dimethyl-2-(methylamino)-4(3H)-pyrimidinone monohydrochloride (interm. 18).

Example 6

80.0 Parts of 1-methyl-1H-imidazol-2-amine monohydrochloride, monohydrate were boiled in 600 parts of phosphoryl chloride. The whole was cooled and the phosphoryl chloride was decanted. The solid residue was heated on a steam bath and 49 parts of methylbenzene were added. After stirring for 30 minutes, 78 parts of 3-acetyl-4,5-dihydro-2(3H)-furanone were added during 20 minutes. Upon completion, stirring was continued for 18 hours. The mixture was quenched by carefully adding 200 parts of water. The mixture was treated with ammonium hydroxide to pH 8. The precipitated product was filtered off, washed with water and crystallized twice from a mixture of dichloromethane, methanol and 1,1'-oxybisethane. The product was filtered off, washed with 1,1'-oxybisethane and dried, yielding 90.2 parts (76.2%) of 6-(2-chloroethyl)-1,7-dimethyl-1H,5H-imidazo[1,2-a]pyrimidin-5-one; mp. 198.2° C. (interm 19).

Example 7 a) To a stirred mixture of 55 parts of intermediate 8, 44.5 parts of sodium carbonate and 135 parts of N,N-dimethylformamide were added 33.5 parts of 1-bromo-3-chloropropane. Stirring was continued overnight at 80°-90° C. After cooling, the reaction mixture was filtered and the filtrate was evaporated. The residue was purified by column chromatography (silica gel; CHCl$_3$/CH$_3$OH 98:2). The eluent of the desired fraction was evaporated and the residue was crystallized from a mixture of methylbenzene and 2,2'-oxybispropane. The product was filtered off and dried, yielding 28 parts (44%) of 6,7,8,9-tetrahydro-3-(2-hydroxyethyl)-2-methyl-9-(phenylmethyl)-4H-pyrimido[1,2-a]pyrimidin-4-one; mp. 150° C. (interm. 20).

b) A mixture of 10 parts of intermediate 20 and 150 parts of an aqueous hydrobromic acid solution 48% was stirred for 6 hours at reflux temperature. The reaction mixture was evaporated and the residue was purified by column chromatography (silica gel; CHCl$_3$/CH$_3$OH 95:5). The eluent of the desired fraction was evaporated and the residue was crystallized from 4-methyl-2-pentanone. The product was filtered off and dried, yielding 5.8 parts (50%) of 3-(2-bromoethyl)-6,7,8,9-tetrahydro-2-methyl-4H-pyrimido[1,2-a]-pyrimidin-4-one monohydrobromide; mp. 223.3° C. (interm. 21).

c) To a stirred mixture of 6 parts of intermediate 20, 2.2 parts of N,N-diethylethanamine and 75 parts of trichloromethane were added dropwise 2.3 parts of methanesulfonyl chloride. Stirring was continued for 1 hour at reflux temperature. After cooling, the reaction mixture was washed with water, dried, filtered and evaporated. The residue was crystallized from a mixture of 2-propanol and 2,2'-oxybispropane. The product was filtered off and dried, yielding 4 parts (63%) of 3-(2-chloroethyl)-6,7,8,9-tetrahydro-2-methyl-9-(phenylmethyl)-4H-pyrimido[1,2-a]pyrimidin-4-one; mp. 114.0° C. (interm. 22)

Example 8 a) To a stirred mixture of 9.2 parts of intermediate 2 and 56.4 parts of N,N-dimethylformamide were added successively 8.5 parts of a solution of sodium methoxide in methanol 30% and 8.6 parts of iodoethane. After stirring for 2 hours at 40° C., the solvent was evaporated and the residue was diluted with 50 parts of water. The product was extracted with trichloromethane (2×74.5 parts) and the combined extracts were dried, filtered and evaporated, yielding 8.5 parts (80.5%) of 3-ethyl-5-(2-hydroxyethyl)-6-methyl-2-(methylamino)-4(3H)pyrimidinone (interm. 23).

b) To a stirred mixture of 8.5 parts of intermediate 23 and 133 parts of trichloromethane were added 16.2 parts of thionyl chloride. After refluxing for 2 hours, the reaction mixture was evaporated and the residue was diluted with 100 parts of water. The solid was filtered off and taken up in water. The whole was basified with ammonium hydroxide. After ½ hour, the solid was filtered off again and dissolved in trichloromethane. This solution was dried, filtered and evaporated, yielding 3.9 parts (42.4%) of 5-(2-chloroethyl)-3-ethyl-6-methyl-2-(methylamino)-4(3H)-pyrimidinone (interm. 24).

Following the same procedure intermediate 2 was also converted into 5-(2-chloroethyl)-6-methyl-2-(methylamino)-3-propyl-4(3H)pyrimidinone (interm. 25).

Example 9 a) To a stirred and cooled (2-propanone-CO$_2$ bath) amount of 35.5 parts of 1-propanamine were added slowly 36 parts of acetic acid, keeping the temperature between −5° C. and 0° C. Next there were added 80.2 parts of intermediate 1 and the mixture was refluxed for 2 hours. After cooling, the reaction mixture was diluted with 300 parts of water and basified with sodium hydroxide. The whole was stirred overnight at room temperature. The product was filtered off, washed with acetonitrile and dried, yielding 63.4 parts (75.0%) of 5-(2-hydroxyethyl)-6-methyl-2-(propylamino)-4(3H)-pyrimidinone (interm. 26).

b) To a stirred mixture of 63.4 parts of intermediate 26 and 376 parts of N,N-dimethylformamide were added 51.0 parts of a solution of sodium methoxide in methanol 30% and, after stirring for ½ hour at room temperature, 42.6 parts of iodomethane. Stirring was continued for 2 hours. The product was filtered off, washed with water (2×) and acetonitrile and dried, yielding 37.6 parts (55.6%) of 5-(2-hydroxyethyl)-3,6-dimethyl-2-

(propylamino)-4(3H)-pyrimidinone; mp. 240° C. (interm. 27).

c) To a stirred mixture of 36 parts of intermediate 27 and 373 parts of trichloromethane were added slowly 48.6 parts of thionyl chloride. After refluxing for 2 hours, the reaction mixture was evaporated. The residue was diluted with 300 parts of water and the whole was basified with sodium hydroxide. The solid was filtered off and dissolved in trichloromethane. This solution was dried, filtered and evaporated and the residue was triturated with acetonitrile. The product was filtered off at 0° C. and dried, yielding 34.8 parts (89.2%) of 5-(2-chloroethyl)-3,6-dimethyl-2-(propylamino)-4(3H)-pyrimidinone; mp. 150° C. (interm. 28). In a similar manner intermediate 1 was also converted into:

5-(2-chloroethyl)-2-[[(4-fluorophenyl)methyl]amino]-3,6-dimethyl-4(3H)pyrimidinone monohydrochloride (interm. 29);

2-(butylamino)-5-(2-chloroethyl)-3,6-dimethyl-4(3H)pyrimidinone; mp. 115° C. (interm. 30); and 5-(2-chloroethyl)-2-(ethylamino)-3,6-dimethyl-4(3H)-pyrimidinone; mp. 160° C. (interm. 31)

and further, following the same procedures 2-dimethylamino-5-(2-hydroxyethyl)-6-methyl-4(3H)-pyrimidinone (Coll. Czech. Chem. Commun., 32, 1582, 1967) was converted into 5-(2-chloroethyl)-2-(dimethylamino)-3,6-dimethyl-4(3H)-pyrimidinone (interm. 32); 5-(2-chloroethyl)-2-(dimethylamino)-6-methyl-3-propyl-4(3H)-pyrimidinone (interm. 33); and 5-(2-chloroethyl)-2-(dimethylamino)-3-ethyl-6-methyl-4(3H)-pyrimidinone monohydrochloride (interm. 34).

Example 10 a) A mixture of 25 parts of 4-methoxybenzenethanamine, 33 parts of intermediate 1, 6.3 parts of acetic acid and 133.2 parts of 1,2-ethanediol was stirred for 4 hours at 150° C. There were added 39 parts of 2-propanol and 9 parts of sodium hydroxide and stirring was continued for 15 min. at 0°-5° C. The product was filtered off, washed with 2-propanol and dried, yielding 30 parts (61.8%) of 5-(2-hydroxyethyl)-2-[[2-(4-methoxyphenyl)ethyl]-amino]-6-methyl-4(3H)-pyrimidinone; mp. 180° C. (interm. 35).

b) A mixture of 30 parts of intermediate 35, 6.5 parts of potassium hydroxide and 77.1 parts of dimethyl sulfoxide was stirred for ½ hour at 70° C. After cooling to 10° C., there were added dropwise 16 parts of iodomethane. The whole was stirred overnight at room temperature and was then poured into 200 parts of water. After stirring for 15 min., the solid was filtered off, washed with water and dissolved in trichloromethane. This solution was dried, filtered and evaporated. The residue was crystallized from 4-methyl-2-pentanone at −10° C. The product was filtered off and dried, yielding 23 parts (72.5%) of 5-(2-hydroxyethyl)-2-[[2-(4-methoxyphenyl)ethyl]amino]-3,6-dimethyl-4(3H)-pyrimidinone; mp. 210° C. (interm. 36).

c) To a stirred mixture of 21 parts of intermediate 36 and 373 parts of trichloromethane were added dropwise 40.5 parts of thionyl chloride. After refluxing for 1 hour and subsequent cooling, the reaction mixture was evaporated. The residue was stirred in acetonitrile at 40° C. The product was filtered off and dried, yielding 21 parts (85.6%) of 5-(2-chloroethyl)-2-[[2-(4-methoxyphenyl)ethyl]amino]-3,6-dimethyl-4(3H)-pyrimidinone monohydrochloride; mp. 185° C. (interm. 37).

In a similar manner there was also prepared 5-(2-chloroethyl)-3,6-dimethyl-2-[(2-pyridinylmethyl)amino]-4(3H)-pyrimidinone dihydrochloride (interm. 38).

Example 11 a) A mixture of 80 parts of intermediate 1, 23 parts of methylhydrazine and 372 parts of 2-ethoxyethanol was stirred for 7 hours at reflux temperature and for 8 hours at room temperature. After cooling to 0° C., the product was filtered off, washed with acetonitrile (2×) and dried, yielding 65 parts (82.0%) of 5-(2-hydroxyethyl)-6-methyl-2-(1-methylhydrazino)-4(3H)-pyrimidinone; mp. 180° C. (interm. 39).

b) To a stirred and heated (40° C.) mixture of 63.4 parts of intermediate 39, 38.2 parts of sodium carbonate and 470 parts of N,N-dimethylformamide were added slowly 33.3 parts of 1-chloropropanone. Stirring was continued for 4 hours at 110° C. and for 8 hours at room temperature. The reaction mixture was filtered and the filtrate was evaporated. The residue was triturated with acetonitrile. The product was filtered off, washed with acetonitrile (2×) and dried, yielding 38 parts (50.3%) of 1,4-dihydro-7-(2-hydroxyethyl)-1,3,8-trimethyl-6H-pyrimido[2,1-c][1,2,4]triazin-6-one; mp. 140° C. (interm. 40).

c) To a stirred mixture of 2.35 parts of intermediate 40 and 74.5 parts of trichloromethane were added 4.9 parts of thionyl chloride. After refluxing for 2 hours, the reaction mixture was evaporated and the residue was triturated with acetonitrile. The product was filtered off and dried, yielding 2.5 parts (98.1%) of 7-(2-chloroethyl)-1,4-dihydro-1,3,8-trimethyl-6H-pyrimido[2,1-c][1,2,4]triazin-6-one; mp. 180° C. (interm. 41).

Example 12 a) To a stirred mixture of 9.9 parts of intermediate 39, 7.41 parts of triethoxymethane and 94 parts of N,N-dimethylformamide were added 3 drops of formic acid. Stirring was continued overnight at 100° C. and for 3 hours at 140° C. The reaction mixture was evaporated and the residue was triturated with acetonitrile. The product was filtered off and dried, yielding 6.8 parts (65.3%) of 6-(2-hydroxyethyl)-1,7-dimethyl-1,2,4-triazolo[4,3-a]-pyrimidin-5(1H)-one; mp. 215° C. (interm. 42).

b) To a stirred mixture of 22.9 parts of intermediate 42 and 596 parts of trichloromethane were added at once 32.4 parts of thionyl chloride. After refluxing for 2 hours, the reaction mixture was evaporated and the residue was triturated in acetonitrile. The product was filtered off at 0° C. and dried, yielding 5.7 parts (99.8%) of 6-(2-chloroethyl)-1,7-dimethyl-1,2,4-triazolo[4,3-a]pyrimidin-5(1H)-one monohydrochloride.; mp. 260° C. (interm. 43). In a similar manner there was also prepared 6-(2-chloroethyl)-1,3,7-trimethyl-1,2,4-triazolo[4,3-a]pyrimidin-5(1H)-one; mp. 140° C. (interm. 44).

Example 13 a) A mixture of 74.7 parts of 1-acetyl-4-(4-fluorobenzoyl)piperidine, 46.5 parts of 1,2-ethanediol, 3 parts of 4-methylbenzenesulfonic acid and 810 parts of benzene was stirred for 108 hours at reflux temperature using a water separator. After cooling, the reaction mixture was washed successively with 250 parts of water, 22.5 parts of ammonium hydroxide and 250 parts of water. The organic layer was dried, filtered and evaporated.

The residue was purified by column chromatography (silica gel; CHCl₃/CH₃COCH₃ 50:50). The eluent of the desired fraction was evaporated, yielding 50 parts (56.8%) of 1-acetyl-4-[2-(4-fluorophenyl)-1,3-dioxolan-2-yl]piperidine (interm. 45).

b) A mixture of 5 parts of intermediate 45 and 100 parts of sodium hydroxide 10% was stirred overnight at reflux temperature. After cooling, the product was extracted with trichloromethane. The extract was dried, filtered and evaporated. The residue was stirred in 2,2'-oxybispropane. The product was filtered off and dried in vacuo at 40° C., yielding 3.5 parts (82%) of 4-[2-(4-fluorophenyl)-1,3-dioxolan-2-yl]piperidine (interm. 46).

c) A mixture of 33 parts of ethyl 4-bromobutanoate, 41 parts of intermediate 46, 35 parts of sodium carbonate and 200 parts of 4-methyl-2-pentanone was stirred for 6 hours at reflux temperature. After cooling, the reaction mixture was filtered and the filtrate was evaporated. The residue was purified by column chromatography (silica gel; CHCl₃/CH₃OH 97:3). The eluent of the desired fraction was evaporated, yielding 59 parts (98%) of ethyl 4-[2-(4-fluorophenyl)-1,3-dioxolan-2-yl]-1-piperidinebutanoate (interm. 47).

d) To a stirred and cooled (ice-bath) mixture of 2.75 parts of sodium ethoxide and 43 parts of 1,2-dimethoxyethane were added dropwise 13 parts of intermediate 47 and 3 parts of ethyl formate. Stirring was continued for 1 hour at 0° C. and overnight at room temperature. The reaction mixture was evaporated and the residue was taken up in water. This solution was neutralized with acetic acid and extracted with 2,2'-oxybispropane. The extract was dried, filtered and evaporated and the residue was crystallized from 2,2'-oxybispropane, yielding 4 parts (28%) of ethyl 4-[2-(4-fluorophenyl)-1,3-dioxolan-2-yl]-α-(hydroxymethylene)-1-piperidinebutanoate; mp. 116.7° C. (interm. 48).

e) To a stirred mixture of 7.2 parts of thiourea, 20 parts of a sodium methoxide solution in methanol 30% and 160 parts of methanol were added 20 parts of intermediate 48. Stirring was continued for 4 hours at reflux temperature. The reaction mixture was evaporated and water was added to the residue. The whole was acidified with acetic acid and extracted with dichloromethane. The extract was dried, filtered and evaporated and the residue was crystallized from 2-propanol. The product was filtered off and dried, yielding 16 parts (70%) of 5-[2-[4-[2-(4-fluorophenyl)-1,3-dioxolan-2-yl]-1-piperidinyl]ethyl]-2-mercapto-4-pyrimidinol acetate (1:1); mp. 182.0° C. (interm. 49).

f) To a stirred suspension of 14 parts of intermediate 49 in 160 parts of methanol were added 11 parts of a sodium methoxide solution in methanol 30%, and after stirring for ½ hour, 4.5 parts of iodomethane. Stirring was continued for 3 hours at reflux temperature. The reaction mixture was evaporated and water was added to the residue. The product was extracted with dichloromethane and the extract was dried, filtered and evaporated. The residue was purified by column chromatography (silica gel; CHCl₃/CH₃OH 15:5). The eluent of the desired fraction was evaporated and the residue was crystallized from 2-propanol. The product was filtered off and dried, yielding 10 parts (80%) of 5-[2-[4-[2-(4-fluorophenyl)-1,3-dioxolan-2-yl]-1-piperidinyl]ethyl]-2-(methylthio)-4-pyrimidinol; mp. 206.1° C. (interm. 50).

g) A mixture of 10.8 parts of intermediate 50 and 3.2 parts of benzenemethanamine was stirred for 2 hours at 190° C. After cooling, the precipitate was filtered off and crystallized from 2-propanol, yielding 11.3 parts (94%) of 5-[2-[4-[2-(4-fluorophenyl)-1,3-dioxolan-2-yl]-1-piperidinyl]ethyl]-2-[(phenylmethyl)amino]-4-pyrimidinol; mp. 245.4° C. (interm. 51).

B. Preparation of Final Compounds

Example 14

A mixture of 3.2 parts of intermediate 22, 2.51 parts of intermediate 46, 2.7 parts of sodium carbonate and 120 parts of 4-methyl-2-pentanone was stirred overnight at reflux temperature. After cooling, the reaction mixture was diluted with water. The organic layer was separated, dried, filtered and evaporated. To the residue there were added 24 parts of hydrochloric acid and 16 parts of ethanol. The whole was stirred for 1 hour at reflux temperature and was then evaporated. The residue was treated with ammonium hydroxide and extracted with trichloromethane. The extract was dried, filtered and evaporated. The residue was purified by column chromatography (silica gel; CHCl₃/CH₃OH 95:5). The eluent of the desired fraction was evaporated and the residue was crystallized from a mixture of 4-methyl-2-pentanone and 2,2'-oxybispropane. The product was filtered off and dried, yielding 1.4 parts (28%) of 3-[2-[4-(4-fluorobenzoyl)-1-piperidinyl]ethyl]-6,7,8,9-tetrahydro-2-methyl-9-(phenylmethyl)-4H-pyrimido[1,2-a]pyrimidin-4-one; mp. 126.0° C. (comp. 75).

Example 15

A mixture of 5.6 parts of intermediate 18, 7.3 parts of 4-[bis(4-fluorophenyl)methylene]piperidine monohydrobromide, 8.5 parts of sodium carbonate, 0.1 parts of potassium iodide and 200 parts of 4-methyl-2-pentanone was stirred overnight at reflux temperature. The reaction mixture was filtered while hot and the filtrate was evaporated. The residue was successively triturated with acetonitrile and recrystallized from 4-methyl-2-pentanone. The product was filtered off and dried, yielding 6.4 parts (68.9%) of 5-[2-[4-[bis(4-fluorophenyl)methylene]-1-piperidinyl]ethyl]-3,6-dimethyl-2-(methylamino)-4(3H)-pyrimidinone; mp. 231.2° C. (comp. 39).

Example 16

A mixture of 11 parts of intermediate 13, 9 parts of 3-(1-piperazinyl)-1,2-benzisoxazole, 5 parts of sodium carbonate, 5 parts of sodium hydrogen carbonate, 0.2 parts of potassium iodide and 160 parts of 1-butanol was stirred for 12 hours at reflux temperature. The reaction mixture was filtered while hot and the filtrate was evaporated. The residue was crystallized from a mixture of acetonitrile and 2-propanol. The product was filtered off and dried in vacuo at 100° C., yielding 14 parts (84.4%) of 2-amino-5-[2-[4-(1,2-benzisoxazol-3-yl)-1-piperazinyl]ethyl]-3,6-dimethyl-4(3H)-pyrimidinone; mp. 201.2° C. (comp. 57).

Example 17

A mixture of 2 parts of intermediate 41, 1.5 parts of 3-(1-piperazinyl)-1H-indazole, 2 parts of sodium carbonate, 0.1 parts of potassium iodide, 81 parts of 1-butanol and 40 parts of 4-methyl-2-pentanone was refluxed for 20 hours. The reaction mixture was filtered while hot and the filtrate was evaporated. The residue was purified by column chromatography (silica gel; CHCl₃/CH₃OH 92:8). The eluent of the desired fraction was evaporated and the residue was crystallized from acetonitrile, yielding 1.7 parts (57.8%) of 1,4-dihydro-7-[2-[4-(1H-indazol-3yl)-1-piperazinyl]ethyl]-1,3,8-trimethyl-6H-pyrimido[2,1-c][1,2,4]triazin-6-one; mp. 198.6° C. (comp. 116).

Example 18

A mixture of 4.4 parts of intermediate 30, 3.3 parts of 6-fluoro-3-(4-piperidinyl)-1,2-benzisoxazole, 4.8 parts of sodium carbonate and 94 parts of N,N-dimethylformamide was stirred overnight at 90° C. The solvent was evaporated and the residue was taken up in 50 parts of water. The product was extracted with trichloromethane (2×74.5 parts) and the combined extracts were dried, filtered and evaporated. The residue was purified by column chromatography (silica gel; CHCl$_3$/CH$_3$OH 90:10). The eluent of the desired fraction was evaporated and the residue was converted into the hydrochloride (1:2) salt in acetonitrile and 2-propanol. The salt was triturated with acetonitrile. The product was filtered off and dried, yielding 4.0 parts (51.8%) of 2-(butylamino)-5-[2-[4-(6-fluoro-1,2-benzisoxazol-3-yl)-1-piperidinyl]ethyl]-3,6-dimethyl-4(3H)-pyrimidinone dihydrochloride; mp. 265.7° C. (comp. 23).

Example 19

To a stirred mixture of 3 parts of compound 57 and 285 parts of trichloromethane were added at once 2 parts of isocyanatobenzene. The mixture was heated to reflux temperature, cooled and evaporated. The residue was crystallized from acetonitrile. The product was filtered off and dried, yielding 4 parts (100%) of N-[5-[2-[4-(1,2-benzisoxazol-3-yl)-1-piperazinyl]-ethyl]-3,4-dihydro-3,6-dimethyl-4-oxo-2-pyrimidinyl]-N'-phenylurea; mp. 216.1° C. (comp. 58).

Example 20

To a stirred mixture of 7.5 parts of intermediate 51, 1.85 parts of sodium carbonate and 45 parts of N,N-dimethylformamide were added dropwise 1.6 parts of 1-chloro-2-propanone. Stirring was continued for 3 hours at 70°-80° C. The reaction mixture was diluted with water and extracted with methylbenzene. The extract was dried, filtered and evaporated. The residue was stirred for 1 hour at reflux temperature with 37.5 parts of a hydrobromic acid solution in acetic acid 48%. After cooling, the product was filtered off and stirred in water. The solution was treated with ammonia and extracted with trichloromethane. The extract was dried, filtered and evaporated. The residue was purified by column chromatography (silica gel; CHCl$_3$/CH$_3$OH 97:3). The eluent of the desired fraction was evaporated and the residue was crystallized from 2-propanol. The product was filtered off and dried, yielding 2.2 parts (30%) of 6-[2-[4-(4-fluorobenzoyl)-1-piperidinyl]ethyl]-2-methyl-1-(phenylmethyl)-5H-imidazo[1,2-a]pyrimidin-5-one; mp. 157.0° C. (comp. 73).

Example 21

A mixture of 1 part of guanidine monohydrochloride, 4 parts of intermediate 48,6 parts of a sodium methoxide solution in methanol 30% and 20 parts of methanol was stirred for 24 hours at reflux temperature. The reaction mixture was evaporated and water was added to the residue. The product was extracted with dichloromethane and the extract was dried, filtered and evaporated. The residue was purified by column chromatography (silica gel; CHCl$_3$/CH$_3$OH 90:10). The eluent of the desired fraction was evaporated and the residue was hydrolyzed with 15 parts of hydrochloric acid 6N in 20 parts of ethanol. The whole was evaporated and the residue was stirred in water. After treatment with ammonium hydroxide, the solid was filtered off and crystallized from 2-propanol, yielding 1.3 parts (37%) of [1-[2-(2-amino-4-hydroxy-5-pyrimidinyl)ethyl]-4-piperidinyl](4-fluorophenyl)methanone; mp. 255.5° C. (comp. 33).

Example 22

A mixture of 2.5 parts of intermediate 51, 30 parts of hydrochloric acid and 20 parts of ethanol was stirred for 4 hours at reflux temperature. After cooling, the precipitate was filtered off and crystallized from methanol. The product was filtered off and dried, yielding 2.3 parts (90%) of (4-fluorophenyl) [1-[2-[4-hydroxy-2-[(phenylmethyl)amino]-5-pyrimidinyl]ethyl]-4-piperidinyl]methanone dihydrochloride; mp. 256.2° C. (comp. 32).

Example 23

A mixture of 2.5 parts of compound 36 and 43.2 parts of acetic anhydride was stirred for 4 hours at reflux temperature. The reaction mixture was evaporated and to the residue there were added 40 parts of water. The whole was treated with ammonium hydroxide and extracted with trichloromethane (2×66.5 parts). The combined extracts were dried, filtered and evaporated and the residue was crystallized from acetonitrile. The product was filtered off at 0° C. and was dried, yielding 1.6 parts (59.1%) of N-[5-[2-[4-[bis(4-fluorophenyl)methylene]-1-piperidinyl]ethyl]-3,4-dihydro-3,6-dimethyl-4-oxo-2-pyrimidinyl]acetamide; mp. 141.0° C. (comp. 55).

Example 24

To a stirred mixture of 2.5 parts of compound 36, 0.44 parts of N,N-diethylethanamine and 399 parts of dichloromethane were added 0.85 parts of benzoyl chloride. The whole was refluxed for 18 hours. After cooling, the reaction mixture was washed with 50 parts of water, dried, filtered and evaporated. The residue was solidified in acetonitrile. The product was filtered off and dried, yielding 2.3 parts (75.4%) of N-[5-[2-[4-[bis(4-fluorophenyl)methylene]-1-piperidinyl]ethyl]-3,4-dihydro-3,6-dimethyl-4-oxo-2-pyrimidinyl]benzamide; mp. 239.6° C. (comp. 56).

All compounds listed in Tables 1 to 6 were prepared following the procedure of the example referred to in the column Ex. No.

TABLE 1

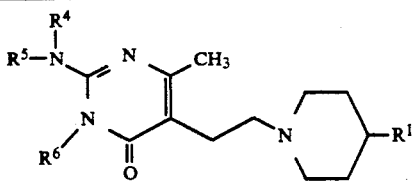

| Comp No. | Ex. No. | R¹ | R⁴ | R⁵ | R⁶ | Physical data mp. |
|---|---|---|---|---|---|---|
| 1 | 15 | CO-(4-F—C₆H₄) | H | H | CH₃ | 205.0° C. |
| 2 | 19 | CO-(4-F—C₆H₄) | H | CO—NH—C₆H₅ | CH₃ | 194.8° C. |
| 3 | 19 | CO-(4-F—C₆H₄) | H | CO—NH—CH₃ | CH₃ | 162.3° C. |
| 4 | 18 | 1H-indol-3-yl | H | H | CH₃ | 284.8° C. |
| 5 | 15 | 6-F-1,2-benzisoxazol-3-yl | H | H | CH₃ | 202.9° C. |
| 6 | 19 | 6-F-1,2-benzisoxazol-3-yl | H | CO—NH—CH₃ | CH₃ | 210.0° C. |
| 7 | 19 | 1H-indol-3-yl | H | CO—NH—C₆H₅ | CH₃ | 207.6° C. |
| 8 | 19 | 1H-indol-3-yl | H | CO—NH—CH₃ | CH₃ | ½H₂O/185.8° C. |
| 9 | 19 | 6-F-1,2-benzisoxazol-3-yl | H | CO—NH—C₆H₅ | CH₃ | 200.1° C. |
| 10 | 18 | 1H-indol-3-yl | CH₃ | H | CH₃ | >300° C.(dec.) |
| 11 | 15 | CO-(4-F—C₆H₄) | CH₃ | H | CH₃ | 179.7° C. |
| 12 | 15 | 6-F-1,2-benzisoxazol-3-yl | CH₃ | H | CH₃ | 165.1° C. |
| 13 | 15 | CO-(4-F—C₆H₄) | CH₂—C₆H₅ | H | CH₃ | 193.6° C. |
| 14 | 18 | 6-F-1,2-benzisoxazol-3-yl | CH₂—C₆H₅ | H | CH₃ | 196.8° C. |
| 15 | 18 | 1H-indol-3-yl | CH₂—C₆H₅ | H | CH₃ | 110.2° C. |
| 16 | 15 | CO-(4-F—C₆H₄) | 2-pyridinylmethyl | H | CH₃ | 157.4° C. |
| 17 | 15 | 6-F-1,2-benzisoxazol-3-yl | (CH₂)₂-(4-OCH₃—C₆H₄) | H | CH₃ | ½ fumarate/179.8° C. |
| 18 | 15 | CO-(4-F—C₆H₄) | (CH₂)₂-(4-OCH₃—C₆H₄) | H | CH₃ | 3/2 fumarate/162.2° C. |
| 19 | 15 | 6-F-1,2-benzisoxazol-3-yl | 2-pyridinylmethyl | H | CH₃ | 188.9° C. |
| 20 | 15 | CO-(4-F—C₆H₄) | CH₂-(4F—C₆H₄) | H | CH₃ | 133.9° C. |
| 21 | 15 | CO-(4-F—C₆H₄) | n-C₃H₇ | H | CH₃ | 120.8° C. |
| 22 | 15 | CO-(4-F—C₆H₄) | n-C₄H₉ | H | CH₃ | 114.8° C. |
| 23 | 18 | 6-F-1,2-benzisoxazol-3-yl | n-C₄H₉ | H | CH₃ | 2HCl/265.7° C. |
| 24 | 18 | 6-F-1,2-benzisoxazol-3-yl | n-C₃H₇ | H | CH₃ | 2HCl/252.2° C. |
| 25 | 18 | 1H-indol-3-yl | n-C₃H₇ | H | CH₃ | 216.2° C. |
| 26 | 15 | CO-(4-F—C₆H₄) | C₂H₅ | H | CH₃ | 143.4° C. |
| 27 | 15 | 6-F-1,2-benzisoxazol-3-yl | CH₂-(4F—C₆H₄) | H | CH₃ | 109.5° C. |
| 28 | 18 | 1H-indol-3-yl | n-C₄H₉ | H | CH₃ | 174.5° C. |
| 29 | 18 | 6-F-1,2-benzisoxazol-3-yl | C₂H₅ | H | CH₃ | 148.8° C. |
| 30 | 18 | 1H-indol-3-yl | C₂H₅ | H | CH₃ | 263.8° C. |
| 31 | 15 | 3-benzo[b]thienyl | CH₃ | H | CH₃ | 164.2° C. |
| 32 | 22 | CO-(4-F—C₆H₄) | CH₂—C₆H₅ | H | H | 2HCl/256.2° C. |
| 33 | 21 | CO-(4-F—C₆H₄) | H | H | H | 255.5° C. |
| 34 | 23 | CO-(4-F—C₆H₄) | H | COCH₃ | CH₃ | 153.5° C. |
| 35 | 23 | 6-F-1,2-benzisoxazol-3-yl | H | COCH₃ | CH₃ | 180.4° C. |

TABLE 2

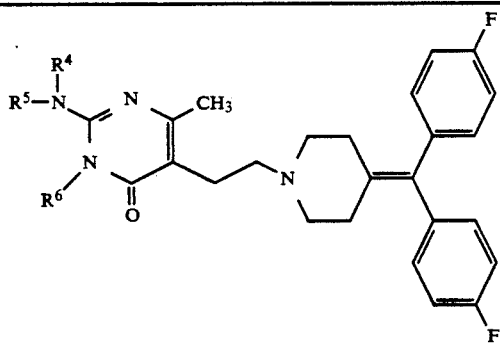

| Comp No. | Ex. No. | R⁴ | R⁵ | R⁶ | Physical data mp. |
|---|---|---|---|---|---|
| 36 | 15 | H | H | CH₃ | 213.4° C. |
| 37 | 19 | H | CO—NH—C₆H₅ | CH₃ | 169.6° C. |
| 38 | 19 | H | CO—NH—CH₃ | CH₃ | 195.6° C. |
| 39 | 15 | CH₃ | H | CH₃ | 231.2° C. |
| 40 | 18 | CH₂—C₆H₅ | H | CH₃ | ½H₂O/106.8° C. |
| 41 | 18 | CH₂-(4F—C₆H₄) | H | CH₃ | 105.7° C. |
| 42 | 15 | n-C₄H₉ | H | CH₃ | 79.9° C. |
| 43 | 15 | n-C₃H₇ | H | CH₃ | 149.1° C. |
| 44 | 15 | C₂H₅ | H | CH₃ | 124.7° C. |
| 45 | 18 | CH₃ | CH₃ | CH₃ | 104.3° C. |
| 46 | 18 | CH₃ | H | n-C₃H₇ | 134.6° C. |
| 47 | 18 | CH₃ | H | C₂H₅ | 149.9° C. |

TABLE 2-continued

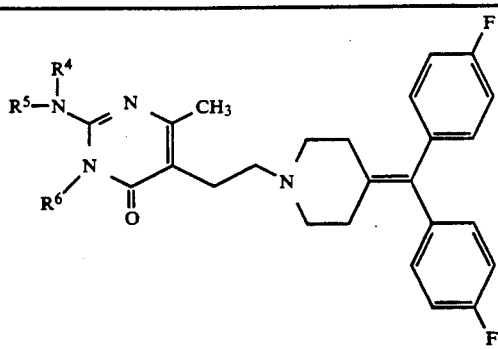

| Comp No. | Ex. No. | R⁴ | R⁵ | R⁶ | Physical data mp. |
|---|---|---|---|---|---|
| 48 | 18 | CH₃ | CH₃ | C₂H₅ | 100.9° C. |
| 49 | 18 | H | H | n-C₃H₇ | 174.6° C. |
| 50 | 18 | CH₃ | CH₃ | n-C₃H₇ | 145.6° C. |
| 51 | 18 | H | H | C₂H₅ | 174.6° C. |
| 52 | 18 | CH₃ | H | CH₂C₆H₅ | 161.3° C. |
| 53 | 18 | CH₃ | CH₃ | CH₂C₆H₅ | 103.1° C. |
| 54 | 18 | H | H | CH₂C₆H₅ | 194.6° C. |
| 55 | 23 | H | COCH₃ | CH₃ | 141.0° C. |
| 56 | 24 | H | COC₆H₅ | CH₃ | 239.6° C. |

TABLE 3

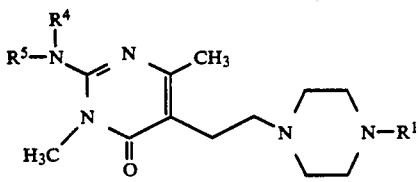

| Comp No. | Ex. No. | R¹ | R⁴ | R⁵ | Physical data mp. |
|---|---|---|---|---|---|
| 57 | 16 | 1,2-benzisoxazol-3-yl | H | H | 201.2° C. |
| 58 | 19 | 1,2-benzisoxazol-3-yl | H | CO—NH—C₆H₅ | 216.1° C. |
| 59 | 19 | 1,2-benzisoxazol-3-yl | H | CO—NH—CH₃ | 211.5° C. |
| 60 | 16 | 1,2-benzisoxazol-3-yl | CH₃ | H | 202.0° C. |
| 61 | 16 | 1,2-benzisoxazol-3-yl | CH₂—C₆H₅ | H | 139.8° C. |
| 62 | 16 | 1,2-benzisoxazol-3-yl | (CH₂)₂-(4-OCH₃—C₆H₄) | H | ½ fumarate/161.0° C. |
| 63 | 17 | 1H-indazol-3-yl | n-C₄H₉ | H | fumarate/203.1° C. |
| 64 | 17 | 1,2-benzisoxazol-3-yl | n-C₃H₇ | H | fumarate/½H₂O/124.6° C. |
| 65 | 17 | 1H-indazol-3-yl | CH₂-(4F—C₆H₄) | H | fumarate/211.2° C. |
| 66 | 16 | 1,2-benzisoxazol-3-yl | 2-pyridinylmethyl | H | 142.9° C. |
| 67 | 16 | 6-F-1H-indazol-3-yl | 2-pyridinylmethyl | H | 254.4° C. |
| 68 | 16 | 6-F-1H-indazol-3-yl | H | H | 284.8° C.(dec.) |
| 69 | 15 | 1,2-benzisoxazol-3-yl | C₂H₅ | H | 178.0° C. |
| 70 | 15 | 1,2-benzisothiazol-3-yl | H | H | 211.5° C. |
| 71 | 15 | 1,2-benzisothiazol-3-yl | n-C₃H₇ | H | HCl/½H₂O/200° C. |
| 72 | 15 | 1,2-benzisothiazol-3-yl | CH₃ | H | 192.7° C. |

TABLE 4

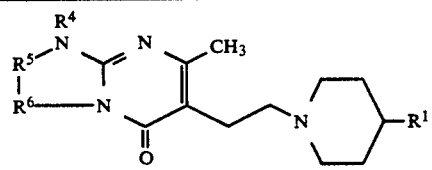

| Comp No. | Ex. No. | R¹ | R⁴ | R⁵—R⁶ | Physical data mp. |
|---|---|---|---|---|---|
| 73 | 20 | CO-(4-F—C₆H₄) | CH₂—C₆H₅ | —C(CH₃)═CH— | 157.0° C. |
| 74 | 14 | CO-(4-F—C₆H₄) | H | —(CH₂)₃— | 197.0° C. |
| 75 | 14 | CO-(4-F—C₆H₄) | CH₂—C₆H₅ | —(CH₂)₃— | 126.0° C. |
| 76 | 15 | 1H-indol-3-yl | CH₃ | —CH═CH— | 260.3° C. |
| 77 | 18 | 6-F-1,2-benzisoxazol-3-yl | CH₃ | —CH═CH— | 238.8° C. |
| 78 | 18 | CO-(4-F—C₆H₄) | CH₃ | —CH═CH— | 199.0° C. |

TABLE 4-continued

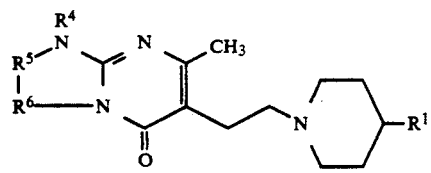

| Comp No. | Ex. No. | R¹ | R⁴ | R⁵—R⁶ | Physical data mp. |
|---|---|---|---|---|---|
| 79 | 18 | CO-(4-F—C₆H₄) | CH₃ | —CH₂—CH₂— | 197.6° C. |
| 80 | 18 | 6-F-1,2-benzisoxazol-3-yl | CH₃ | —CH₂—CH₂— | 234.4° C. |
| 81 | 15 | CO-(4-F—C₆H₄) | CH₃ | —C(CH₃)=CH— | 195.6° C. |
| 82 | 18 | 6-F-1,2-benzisoxazol-3-yl | CH₃ | —C(CH₃)=CH— | 200.7° C. |
| 83 | 18 | 1H-indol-3-yl | CH₃ | —C(CH₃)=CH— | 243.8° C. |
| 84 | 15 | CO-(4-F—C₆H₄) | CH₂—C₆H₅ | —C(CH₃)=CH— | 153.2° C. |
| 85 | 15 | CO-(4-F—C₆H₄) | CH₃ | —N=C(CH₃)—CH₂— | 160.5° C. |
| 86 | 18 | 6-F-1,2-benzisoxazol-3-yl | CH₃ | —N=C(CH₃)—CH₂— | 180.2° C. |
| 87 | 15 | CO-(4-F—C₆H₄) | CH₃ | —N=C(CH₃)— | 193.9° C. |
| 88 | 18 | 6-F-1,2-benzisoxazol-3-yl | CH₃ | —N=C(CH₃)— | 219.1° C. |
| 89 | 18 | 6-F-1,2-benzisoxazol-3-yl | CH₃ | —N=CH— | 188.8° C. |
| 90 | 15 | CO-(4-F—C₆H₄) | CH₃ | —(CH₂)₃— | 169.3° C. |
| 91 | 18 | 6-F-1,2-benzisoxazol-3-yl | CH₃ | —(CH₂)₃— | 202.1° C. |
| 92 | 15 | 6-F-benzofuran-3-yl | CH₃ | —C(CH₃)=CH— | 234.4° C. |
| 93 | 15 | 6-F-1H-indazol-3-yl | CH₃ | —C(CH₃)=CH— | 230.3° C. |
| 94 | 15 | 6-F-benzofuran-3-yl | CH₃ | —CH₂—CH₂— | 200.5° C. |
| 95 | 18 | 6-F-1,2-benzisoxazol-3-yl | CH₃ | —C(C₆H₅)=CH— | 187.9° C. |
| 96 | 15 | CO-(4-F—C₆H₄) | CH₃ | —C(C₆H₅)=CH— | 184.9° C. |
| 97 | 15 | 1-benzyl-1H-indol-3-yl | CH₃ | —CH=CH— | 131.5° C. |
| 98 | 15 | 1-benzyl-6-F-1H-indazol-3-yl | CH₃ | —CH=CH— | 158.6° C. |
| 99 | 15 | 1-benzyl-1H-indol-3-yl | CH₃ | —C(CH₃)=CH— | 149.5° C. |
| 100 | 15 | 1-benzyl-6-F-1H-indazol-3-yl | CH₃ | —CH₂—CH₂— | 165.0° C. |
| 101 | 15 | 1-benzyl-1H-indol-3-yl | CH₃ | —CH₂—CH₂— | 158.7° C. |
| 102 | 15 | 1-benzyl-6-F-1H-indazol-3-yl | CH₃ | —C(CH₃)=CH— | 252.0° C. |

TABLE 5

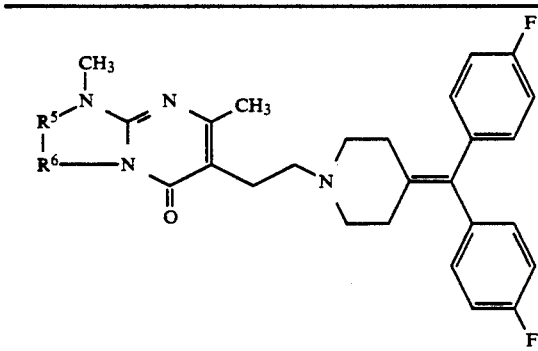

| Comp No. | Ex. No. | R⁵—R⁶ | Physical data mp. |
|---|---|---|---|
| 103 | 15 | —CH=CH— | 184.1° C. |
| 104 | 18 | —CH₂—CH₂— | 2HCl/253.5° C. |
| 105 | 15 | —C(CH₃)=CH— | 90.0° C. |
| 106 | 15 | —N=C(CH₃)—CH₂— | 169.8° C. |
| 107 | 15 | —N=C(CH₃)— | 144.1° C. |
| 108 | 18 | —CH₂—CH₂—CH₂— | 173.2° C. |
| 109 | 15 | —C(C₆H₅)=CH— | 184.8° C. |

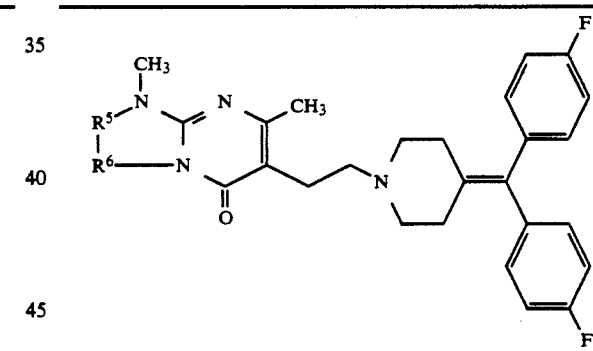

TABLE 6

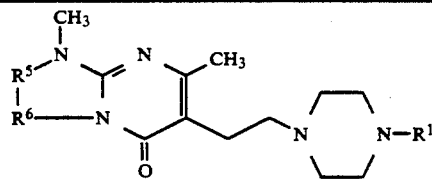

| Comp No. | Ex. No. | R¹ | R⁵—R⁶ | Physical data mp. |
|---|---|---|---|---|
| 110 | 15 | 1,2-benzisoxazol-3-yl | —CH=CH— | 235.1° C. |
| 111 | 16 | 1,2-benzisoxazol-3-yl | —C(CH₃)=CH— | 201.3° C. |
| 112 | 15 | 1,2-benzisoxazol-3-yl | —N=C(CH₃)—CH₂— | 179.6° C. |
| 113 | 15 | 1,2-benzisoxazol-3-yl | —N=C(CH₃)— | 169.4° C. |
| 114 | 15 | 1,2-benzisoxazol-3-yl | —N=CH— | >180° C.(dec.) |

TABLE 6-continued

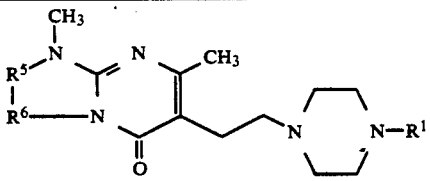

| Comp No. | Ex. No. | $R^1$ | $R^5-R^6$ | Physical data mp. |
|---|---|---|---|---|
| 115 | 15 | 1,2-benzisoxazol-3-yl | $-CH_2-CH_2-$ | >240° C.(dec.) |
| 116 | 17 | 1H-indazol-3-yl | $-N=C(CH_3)-CH_2-$ | 198.6° C. |
| 117 | 17 | 6-F-1H-indazol-3-yl | $-CH=CH-$ | 249.8° C. |
| 118 | 17 | 1H-indazol-3-yl | $-C(CH_3)=CH-$ | 240.7° C. |
| 119 | 17 | 1H-indazol-3-yl | $-CH=CH-$ | 234.9° C. |
| 120 | 15 | 1,2-benzisoxazol-3-yl | $-CH_2-CH_2-CH_2-$ | 204.8° C. |
| 121 | 15 | 1H-indazol-3-yl | $-CH_2-CH_2-CH_2-$ | 225.4° C. |
| 122 | 15 | 1,2-benzisothiazol-3-yl | $-CH_2-CH_2-$ | 183.1° C. |
| 123 | 15 | 1,2-benzisothiazol-3-yl | $-C(CH_3)=CH-$ | 159.9° C. |
| 124 | 15 | 1,2-benzisothiazol-3-yl | $-CH=CH-$ | 169.3° C. |
| 125 | 15 | 1,2-benzisoxazol-3-yl | $-C(C_6H_5)=CH-$ | 196.0° C. |
| 126 | 15 | 1H-indazol-3-yl | $-C(C_6H_5)=CH-$ | 269.3° C. |

C) Pharmacological Examples

The useful sleep-enhancing properties of the compounds of the first subgroup wherein $R^1$ is a radical of formula (a-4) and X is C, said compounds being exemplified in tables 2 and 5 can clearly be demonstrated in the following test procedure.

Example 25

Sleep-wakefulness patterns in the rat

Under pentobarbital anesthesia (50 mg/kg i.p.) 10 adult male Wistar rats weighing 240 to 260 g were chronically implanted for standard polygraphic recording of electroencephalogram (EEG), electro-oculogram (EOG) and electromyogram (EMG). After a 8–10 day recovery period from surgery and habituation to the recording conditions (12 h light-dark schedule, light on at 9:00 a.m.), pharmacological tests were started.

The animals received 0.04, 0.16 or 0.63 mg/kg of compound 39 dissolved in 1 mM tartaric acid and injected i.p. at the onset of the light period. A minimum of 3 recovery days was allowed between two treatments.

Polygraphic recordings were scored visually and classified as being either wakefulness (W), light slow wave sleep (SWS1), deep slow wave sleep (SWS2) or paradoxical sleep (PS). Sleep-wakefulness parameters were analyzed for each of the two successive 4 h periods following the treatment and compared to baseline (vehicle injection under the same conditions). The amounts of sleep and wakefulness states were expressed as percentage of baseline recordings which represented means of two baseline values per animal. Statistical tests were performed by means of the two-tailed Student t-test.

Dose-response effects of compound 39

The administration of compound 39 (0.04 to 0.63 mg/kg) at the onset of the light period induced a dose-dependent increase of SWS2 combined with a dose-related deficit in W, SWS1 and PS throughout the 8 h recording period. Significant effects were observed from the lowest dose upwards. Sleep-wakefulness changes occurred mainly during the first 4 h period following the treatment but persisted into the second 4 h period.

As shown in Table 7, the SWS2-increasing effect of compound 39 was due to a marked prolongation of SWS2 episodes, whereas the number of episodes was reduced. For each of the other states (W, SWS1, and PS) the number of episodes was also decreased while their mean duration rather tended to be enhanced.

Comparison with Ritanserin Effects

Dose-response effects of 6-[2-[4-[bis(4-fluorophenyl)-methylene]-1-piperidinyl]ethyl]-7-methyl-5H-thiazolo[3,2-a]pyrimidin-5-one, which is generically known as ritanserin (0.04 to 2.5 mg/kg) have been previously analyzed in a separated group of 8 rats (Dugovic C., Wauquier A., Leysen J. E., Marrannes R. and Janssen P. A. J., Psychopharmacology, 97: 436–442, 1989). At the dose of 0.63 mg/kg ritanserin induced a significant increase of SWS2 for 8 h at the expense of W, SWS1 and PS.

Conversely, doses of 0.04 and 0.16 mg/kg of ritanserin produced no major effects on sleep-wakefulness patterns, whereas the same doses of compound 39 induced a significant sleep-wakefulness response. Thus, compound 39 was effective at a 10-fold lower dose than that of ritanserin. Moreover, a clear dose-related response was obtained with compound 39 but not with ritanserin.

TABLE 7

Dose-response effects of compound 39 on the number of episodes and mean duration of sleep-wakefulness states during the two consecutive 4 h periods following treatment. Values are means ± SEM of 10 rats.

| | | Compound 39 (mg/kg i.p.) | | | |
|---|---|---|---|---|---|
| | | 0 | 0.04 | 0.16 | 0.63 |
| | | NUMBER OF EPISODES | | | |
| W | 0–4 h | 27 ± 2 | 26 ± 3 | 23 ± 1 | 22 ± 1 |
| | 4–8 h | 27 ± 2 | 26 ± 2 | 23 ± 2 | 26 ± 2 |
| SWS1 | 0–4 h | 38 ± 2 | 33 ± 3 | 28 ± 2 | 26 ± 2 |
| | 4–8 h | 44 ± 2 | 35 ± 3 | 35 ± 2 | 34 ± 2 |
| SWS2 | 0–4 h | 37 ± 2 | 32 ± 3 | 27 ± 2 | 27 ± 2 |
| | 4–8 h | 50 ± 2 | 41 ± 3 | 39 ± 2 | 40 ± 2 |
| PS | 0–4 h | 6 ± 1 | 4 ± 1 | 3 ± 1 | 3 ± 1 |
| | 4–8 h | 16 ± 1 | 13 ± 1 | 12 ± 1 | 12 ± 1 |
| | | MEAN DURATION OF EPISODES (min.) | | | |
| W | 0–4 h | 2.8 ± 0.3 | 2.6 ± 0.3 | 2.9 ± 0.3 | 2.7 ± 0.2 |
| | 4–8 h | 1.8 ± 0.1 | 2.0 ± 0.2 | 2.0 ± 0.3 | 1.9 ± 0.2 |
| SWS1 | 0–4 h | 0.8 ± 0.0 | 0.8 ± 0.0 | 0.9 ± 0.0 | 0.8 ± 0.0 |
| | 4–8 h | 0.7 ± 0.0 | 0.7 ± 0.0 | 0.7 ± 0.0 | 0.7 ± 0.0 |

TABLE 7-continued

Dose-response effects of compound 39 on the number of episodes and mean duration of sleep-wakefulness states during the two consecutive 4 h periods following treatment. Values are means ± SEM of 10 rats.

| | | Compound 39 (mg/kg i.p.) | | | |
|---|---|---|---|---|---|
| | | 0 | 0.04 | 0.16 | 0.63 |
| SWS2 | 0–4 h | 3.6 ± 0.2 | 4.7 ± 0.5 | 5.8 ± 0.5 | 5.9 ± 0.4 |
| | 4–8 h | 2.8 ± 0.2 | 3.5 ± 0.2 | 3.9 ± 0.3 | 3.7 ± 0.2 |
| PS | 0–4 h | 1.5 ± 0.1 | 2.1 ± 0.2 | 2.0 ± 0.3 | 2.2 ± 0.4 |
| | 4–8 h | 1.8 ± 0.1 | 1.9 ± 0.1 | 2.1 ± 0.1 | 2.1 ± 0.1 |

Example 26

The useful neuroleptic properties of the second subgroup of compounds of formula (I) wherein $R^1$ is a radical of formula (a-1), (a-2) or (a-3) and X is CH or X is N in case $R^1$ is a radical of formula (a-2), said compounds being exemplified in Tables 1, 3, 4 and 6, can clearly be demonstrated in the "Combined Apomorphine, Tryptamine and Norepinephrine test in rats" which is described in Arch. Int. Pharmacodyn. Ther., 227, 238–253, 1977. Further the activity of the subject compounds as serotonin antagonists is evidenced by the experimental data obtained in the "Gastric Lesions induced by compound 48/80 in rats" test, described in U.S. Pat. No. 4,335,127. Antihistaminic activity can be demonstrated by, e.g. the results obtained in the "Protection of Rats from compound 48/80 induced lethality" test, described in U.S. Pat. No. 4,556,660. All tests were carried out following the procedures described in the cited references and the experimental data are shown in Table 8.

TABLE 8

| Co. No. | Combined ATN test in rats $ED_{50}$ values in mg/kg bodyweight | | | | Compound 48/80 tests $ED_{50}$ values in mg/kg bodyweight | |
|---|---|---|---|---|---|---|
| | (APO) | (TRY) convulsions | (TRY) hyperaemia | (NOR) | Gastric lesions | Lethality |
| 19 | 0.08 | 0.31 | 0.0025 | 0.08 | 0.04 | 0.04 |
| 34 | 0.31 | 0.31 | 0.005 | 1.25 | 0.04 | 0.04 |
| 69 | 0.08 | 0.31 | 0.00125 | 0.31 | 0.00125 | 0.02 |
| 71 | 0.08 | 0.08 | 0.005 | 1.25 | 0.63 | 0.16 |
| 77 | 0.04 | 0.04 | ≦0.00063 | 0.16 | 0.04 | 0.005 |
| 80 | 0.08 | 0.08 | 0.00125 | 0.31 | 0.04 | 0.005 |
| 86 | 0.04 | 0.04 | 0.00125 | 0.08 | 0.02 | 0.02 |
| 88 | 0.08 | 0.08 | 0.00125 | 0.16 | 0.04 | 0.16 |
| 89 | 0.08 | 0.08 | ≦0.0025 | 0.31 | 0.16 | 0.02 |
| 111 | 0.08 | 0.31 | 0.005 | 0.31 | 0.16 | 0.005 |
| 112 | 0.08 | 0.31 | 0.005 | 0.63 | 0.04 | 0.16 |
| 113 | 0.08 | 0.31 | 0.005 | 1.25 | 0.08 | 0.31 |
| 114 | 0.08 | 0.31 | ≦0.04 | 1.25 | 0.16 | 0.08 |
| 115 | 0.08 | 0.31 | 0.005 | 1.25 | 0.02 | 0.04 |
| 120 | 0.02 | 0.08 | 0.02 | 1.25 | 0.63 | 0.01 |
| 124 | 0.08 | 0.02 | 0.00125 | 5 | 0.04 | 0.31 |

D) Composition Examples

The following formulations exemplify typical pharmaceutical compositions in dosage unit form suitable for systemic administration to warm-blooded animals in accordance with the present invention.

"Active ingredient" (A.I.) as used throughout these examples relates to a compound of formula (I), a pharmaceutically acceptable acid addition salt or a stereochemically isomeric form thereof.

Example 27

Oral Drops 500 g of the A.I. is dissolved in 0.5 l of 2-hydroxypropanoic acid and 1.5 l of the polyethylene glycol at 60°~80° C. After cooling to 30°~40° C. there are added 35 l of polyethylene glycol and the mixture is stirred well. Then there are added a solution of 1750 g of sodium saccharin in 2.5 l of purified water and while stirring there are added 2.5 l of cocoa flavor and polyethylene glycol q.s. to a volume of 50 l, providing an oral drop solution comprising 10 mg/ml of the A.I. The resulting solution is filled into suitable containers.

Example 28

Oral Solutions 9 g of methyl 4-hydroxybenzoate and 1 g of propyl 4-hydroxybenzoate are dissolved in 4 l of boiling purified water. In 3 l of this solution are dissolved first 10 g of 2,3-dihydroxybutanedioic acid and thereafter 20 g of the A.I. The latter solution is combined with the remaining part of the former solution and 12 l of 1,2,3-propanetriol and 3 l of sorbitol 70% solution are added thereto. 40 g of sodium saccharin are dissolved in 0.5 l of water and 2 ml of raspberry and 2 ml of gooseberry essence are added. The latter solution is combined with the former, water is added q.s. to a volume of 20 l providing an oral solution comprising 5 mg of the A.I. per teaspoonful (5 ml). The resulting solution is filled in suitable containers.

Example 29

Capsules 20 g of the A.I., 6 g sodium lauryl sulfate, 56 g starch, 56 g lactose, 0.8 g colloidal silicon dioxide, and 1.2 g magnesium stearate are vigorously stirred together. The resulting mixture is subsequently filled into 1000 suitable hardened gelatin capsules, each comprising 20 mg of the A.I..

Example 30

Film-Coated Tablets

Preparation of tablet core

A mixture of 100 g of the A.I., 570 g lactose and 200 g starch is mixed well and thereafter humidified with a solution of 5 g sodium dodecyl sulfate and 10 g polyvinylpyrrolidone (Kollidon-K 90 ®) in about 200 ml of water. The wet powder mixture is sieved, dried and sieved again. Then there is added 100 g microcrystalline cellulose (Avicel ®) and 15 g hydrogenated vegetable oil (Sterotex ®). The whole is mixed well and compressed into tablets, giving 10.000 tablets, each comprising 10 mg of the active ingredient.

Coating

To a solution of 10 g methyl cellulose (Methocel 60 HG ®) in 75 ml of denatured ethanol there is added a solution of 5 g of ethyl cellulose (Ethocel 22 cps ®) in 150 ml of dichloromethane. Then there are added 75 ml of dichloromethane and 2.5 ml 1,2,3-propanetriol. 10 g of polyethylene glycol is molten and dissolved in 75 ml of dichloromethane. The latter solution is added to the former and then there are added 2.5 g of magnesium octadecanoate, 5 g of polyvinylpyrrolidone and 30 ml of concentrated colour suspension (Opaspray K-1-2109 ®) and the whole is homogenated. The tablet cores are coated with the thus obtained mixture in a coating apparatus.

Example 31

Injectable Solutions 1.8 g methyl 4-hydroxybenzoate and 0.2 g propyl 4-hydroxybenzoate are dissolved in about 0.5 l of boiling water for injection. After cooling to about 50° C. there are added while stirring 4 g lactic acid, 0.05 g propylene glycol and 4 g of the A.I.. The solution is cooled to room temperature and supplemented with water for injection q.s. ad 1 l volume, giving a solution of 4 mg A.I. per ml. The solution is sterilized by filtration (U.S.P. XVII p. 811) and filled in sterile containers.

Example 32

Suppositories 3 g A.I. is dissolved in a solution of 3 g 2,3-dihydroxybutanedioic acid in 25 ml polyethylene glycol 400. 12 g surfactant (SPAN ®) and triglycerides (Witepsol 555 ®) q.s. ad 300 g are molten together. The latter mixture is mixed well with the former solution. The thus obtained mixture is poured into moulds at a temperature of 37°-38° C. to form 100 suppositories each containing 30 mg of the A.I.

We claim:

1. A compound of the formula:

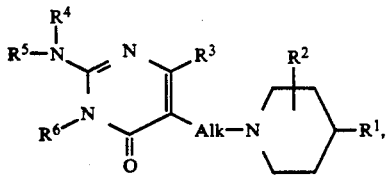

a pharmaceutically acceptable acid addition salt thereof, or a stereochemically isomeric form thereof, wherein:

$R^1$ is a radical of the formula:

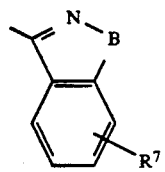

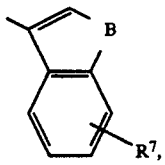

wherein:

$R^7$ is hydrogen, $C_{1-4}$alkyl or halo; and
B is O, S or $NR^8$ wherein $R^8$ is hydrogen, $C_{1-4}$alkyl or $ArC_{1-4}$alkyl;

$R^2$ is hydrogen or $C_{1-6}$alkyl;
Alk is $C_{1-6}$alkanediyl;
$R^3$ is hydrogen or $C_{1-6}$alkyl;
$R^4$ is hydrogen, $C_{1-6}$alkyl optionally substituted with $C_{1-6}$alkyloxy, Ar, pyridinyl, furanyl or 5-methyl-2-furanyl; and
$R^5$ and $R^6$ taken together form a bivalent radical of the formula:

| | |
|---|---|
| $-CH_2-CH_2-$ | (b-1); |
| $-CH_2-CH_2-CH_2-$ | (b-2); |
| $-CH=CH-$ | (b-3); |
| $-CH=N-$ | (b-4); |
| $-N=CH-$ | (b-5); | or

| | |
|---|---|
| $-N=CH-CH_2-$ | (b-6), | wherein one or where possible two hydrogen atoms of said radicals (b-1) to (b-6) each independently from one another may be replaced by $C_{1-6}$alkyl; or wherein one hydrogen atom of radical (b-3) may be replaced by phenyl;
wherein in the foregoing each Ar independently is phenyl or phenyl substituted with 1, 2 or 3 substituents each independently selected from the group consisting of halo, hydroxy, nitro, cyano, trifluoromethyl, $C_{1-6}$alkyl, $C_{1-6}$alkyloxy, $C_{1-6}$alkylthio, mercapto, amino, mono- and di($C_{1-6}$alkyl)amino, carboxyl, $C_{1-6}$alkyloxycarbonyl and $C_{1-6}$alkylcarbonyl.

2. A compound according to claim 1 wherein:
$R^2$ is hydrogen;
Alk is $C_{2-4}$alkanediyl;
$R^3$ is $C_{1-4}$alkyl;
$R^4$ is hydrogen, $C_{1-6}$alkyl optionally substituted with Ar or pyridinyl;
$R^5$ and $R^6$ taken together form a bivalent radical of formula (b-1) to (b-6) wherein one hydrogen atom of said radicals (b-1) to (b-6) may be replaced by $C_{1-6}$alkyl, or wherein one hydrogen atom of radical (b-3) may be replaced by phenyl;
$R^7$ is hydrogen or halo; and
each Ar independently is phenyl optionally substituted with 1 or 2 substituents each independently selected from the group consisting of halo, hydroxy, nitro, cyano, trifluoromethyl, $C_{1-6}$alkyl and $C_{1-6}$alkyloxy.

3. A compound according to claim 2 wherein:
$R^3$ is methyl;
$R^4$ is hydrogen, $C_{1-6}$alkyl, phenylmethyl or pyridinylmethyl;

R⁵ and R⁶ taken together form a bivalent radical of formula (b-1), (b-2), (b-3), (b-5) or (b-6), wherein one hydrogen atom of said radicals (b-3), (b-5) or (b-6) may be replaced by methyl, or wherein one hydrogen atom of radical (b-3) may be replaced by phenyl;

R⁷ is hydrogen or fluoro; and each Ar independently is phenyl optionally substituted with halo or $C_{1-6}$alkyloxy.

4. A compound according to claim 3 wherein R⁵ and R⁶ taken together form a radical of the formula —CH=CH—, —CH₂—CH₂— or —CH₂—CH₂—CH₂—.

5. A compound according to claim 4 wherein said compound is selected from the group consisting of:

6-[2-[4-(6-fluoro-1,2-benzisoxazol-3-yl)-1-piperidinyl]ethyl]-1,7-dimethylimidazo[1,2-a]pyrimidin-5(1H)-one;

6-[2-[4-(6-fluoro-1,2-benzisoxazol-3-yl)-1-piperidinyl]ethyl]-2,3-dihydro-1,7-dimethylimidazo[1,2-a]pyrimidin-5(1H)-one; and 3-[2-[4-(6-fluoro-1,2-benzisoxazol-3-yl)-1-piperidinyl]ethyl]-6,7,8,9-tetrahydro-2,9-dimethyl-4H-pyrimido[1,2-a]pyrimidin-4-one.

6. A pharmaceutical composition comprising an inert carrier and as an active ingredient an effective amount of a compound as claimed in any of claims 1–5.

7. A method of treating warm-blooded animals suffering from diseases associated with the release of neurotransmitters, which comprises the administration thereto of an effective amount of a compound as claimed in any of claims 1–5.

8. A method of treating warm-blooded animals suffering from psychotic diseases, which comprises the administration thereto of an effective antipsychotic amount of a compound as claimed in any of claims 2–5.

* * * * *